US012686875B2

(12) United States Patent
Riesenberg et al.

(10) Patent No.: US 12,686,875 B2
(45) Date of Patent: Jul. 21, 2026

(54) SMALL MOLECULES FOR INCREASING PRECISE GENOME EDITING EFFICIENCY

(71) Applicant: Max-Planck-Gesellschaft zur Förderung der Wissenschaften e.V., Munich (DE)

(72) Inventors: Stephan Riesenberg, Jena (DE); Tomislav Maricic, Leipzig (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 1207 days.

(21) Appl. No.: 17/416,949

(22) PCT Filed: Dec. 19, 2019

(86) PCT No.: PCT/EP2019/086316

§ 371 (c)(1),
(2) Date: Jun. 21, 2021

(87) PCT Pub. No.: WO2020/127738

PCT Pub. Date: Jun. 25, 2020

(65) Prior Publication Data

US 2022/0154220 A1 May 19, 2022

(30) Foreign Application Priority Data

Dec. 21, 2018 (EP) .................................... 18215071

(51) Int. Cl.

*C12N 15/90* (2006.01)
*A61K 31/165* (2006.01)
*A61K 31/194* (2006.01)
*A61K 31/519* (2006.01)
*A61K 31/5377* (2006.01)
*A61K 45/06* (2006.01)
*A61P 43/00* (2006.01)

(52) U.S. Cl.

CPC ............ *C12N 15/90* (2013.01); *A61K 31/165* (2013.01); *A61K 31/194* (2013.01); *A61K 31/519* (2013.01); *A61K 31/5377* (2013.01); *A61K 45/06* (2013.01); *A61P 43/00* (2018.01); *C12N 15/902* (2013.01)

(58) Field of Classification Search

CPC .............................. C12N 15/90; C12N 15/902
See application file for complete search history.

(56) References Cited

U.S. PATENT DOCUMENTS

2014/0242702 A1 8/2014 Chen et al.
2017/0290836 A1 10/2017 Fuchss et al.

FOREIGN PATENT DOCUMENTS

CN 108686221 A 10/2018
EP 3388517 A1 10/2018
EP 3489357 A1 5/2019
WO 2006135721 A1 12/2006
WO 2017147056 A1 8/2017
WO 2018189186 A1 10/2018
WO 2019224603 A1 11/2019

OTHER PUBLICATIONS

Sullivan et al. (2016) Identification of a Small Molecule Inhibitor of RAD52 by Structure-Based Selection. PLoS ONE 11(1): e0147230. (Year: 2016).*

C. Robert et al. Histone deacetylase inhibitors decrease NHEJ both by acetylation of repair factors and trapping of PARP1 at DNA double-strand breaks in chromatin. Leukemia Research, 45 (2016) 14-23. (Year: 2016).*

Barrangou et al. Applications of CRISPR technologies in research and beyond. Nature Biotechnology, vol. 4, No. 9, Sep. 2016. (Year: 2016).*

Lemos et al. CRISPR/Cas9 cleavages in budding yeast reveal templated insertions and strand-specific insertion/deletion profiles. PNAS. E2040-E2047, vol. 115, No. 9. Published online Feb. 13, 2018. (Year: 2018).*

Harnor et al. Targeting DNA-Dependent Protein Kinase for Cancer Therapy. ChemMedChem 2017, 12, 895-900. Published May 29, 2017 (Year: 2017).*

Prakash et al. Clinically Applicable Inhibitors Impacting Genome Stability. Molecules 2018, 23, 1166, pp. 1-66. Published May 13, 2018. (Year: 2018).*

European Office Action issued in application No. 9 828 736.9 dated Apr. 26, 2023, 9 pgs.

Suzannah J. Harnor et al: Targeting DNA-Dependent Protein Kinase for Cancer Therapy, ChemMedChem, vol. 12, No. 12, May 29, 2017, pp. 895-900.

Daniel Kranser et al., "Increasing HR-Mediated Genome Editing in HSPCs through Manipulation of DNA Repair Proteins", Molecular Therapy, vol. 26, No. 5 (suppl 1), May 1, 2018, p. 84.

Meena Shrivastav et al.:, "Regulation of DNA double-strand break repair pathway choice", Cell Research—Kibao Yanjiu, vol. 18, No. 1, Jan. 1, 2008, pp. 134-147.

Stephan Riesenberg et al., Abstract, "Simultaneous precise editing of multiple genes in human cells" Nucleic Acids Research Advance Access, vol. 47, No. 19, Aug. 8, 2019 , pp. e116-e116.

Johanna C Bendell et al:, "Phase 1, open-label, dose-escalation study of M3814 + avelumab radiotherapy (RT) in patients (pts) with advanced solid tumors", Journal of Clinical Oncology, vol. 37, No. 15S, May 20, 2019, p. TPS3169.

International Search Report issued in PCT/EP2019/086316 dated Mar. 13, 2020, 4 pages.

(Continued)

*Primary Examiner* — Arthur S Leonard
*Assistant Examiner* — Nicholas A Humphries
(74) *Attorney, Agent, or Firm* — Rothwell, Figg, Ernst & Manbeck, P.C.

(57) ABSTRACT

The present invention relates to compounds suitable to increase precise genome editing efficiency in a eukaryotic target cell or target organism. Thus, the present invention can be applied in gene therapy.

27 Claims, 6 Drawing Sheets

Figure 1:
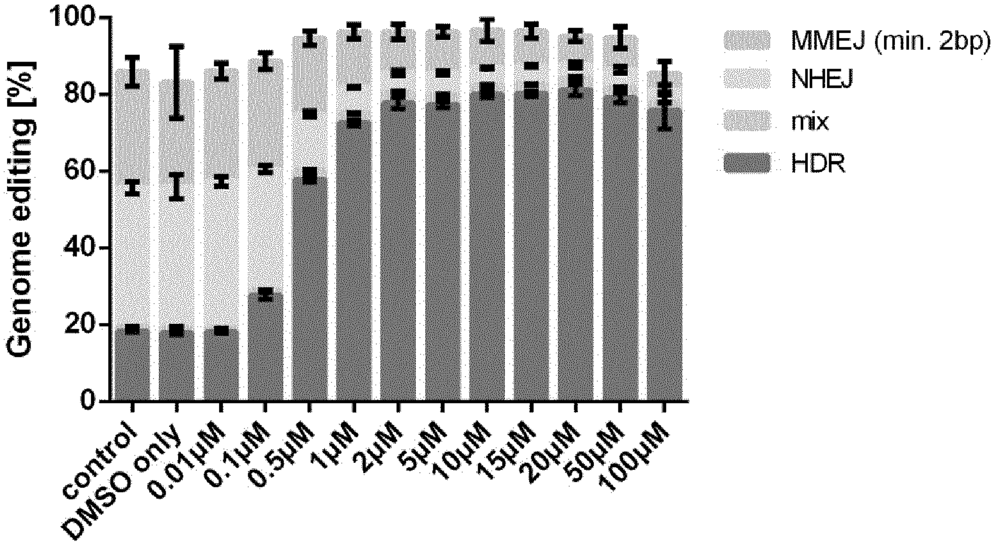

Specification includes a Sequence Listing.

(56) References Cited

OTHER PUBLICATIONS

Office action issued Oct. 28, 2024 in CA 3,128,085, 5 pages.
Chu et al., "Increasing the efficiency of homology-directed repair for CRISPR-Cas9-induced precise gene editing in mammalian cells", Nat Biotechnol 33, 543-548 (2015).
Fu et al., "High-frequency off-target mutagenesis induced by CRISPR-Cas nucleases in human cells", Nat Biotechnol 31, 822-826 (2013).
Dueva and Iliakis, "Alternative pathways of non-homologous end joining (NHEJ) in genomic instability and cancer", Transl Cancer Res 2, 163-177 (2013).
Gonzalez et al., "An iCRISPR Platform for Rapid, Multiplexable, and Inducible Genome Editing in Human Pluripotent Stem Cells", Cell Stem Cell 15, 215-226 (2014).
Greco et al., "SCR7 is neither a selective nor a potent inhibitor of human DNA ligase IV", DNA Repair 43, 18-23 (2016).
Grimme et al., "Human Rad52 binds and wraps single-stranded DNA and mediates annealing via two hRad52-ssDNA complexes", Nucleic Acids Res 38, 2917-2930 (2010).
Huang et al., "Identification of Specific Inhibitors of Human RAD51 Recombinase Using High-Throughput Screening", ACS Chem Biol 6, 628-635 (2011).
Kent et al., "The Human Genome Browser at UCSC", Genome Res 12, 996-1006 (2002).
Kim et al., "Genome-wide analysis reveals specificities of Cpf1 endonucleases in human cells", Nat Biotechnol 34, 863-868 (2016).
Kircher et al., "Double indexing overcomes inaccuracies in multiplex sequencing on the Illumina platform", Nucleic Acids Res 40, e3, 8 pages (2012).
Kleinstiver et al., "Genome-wide specificities of CRISPR-Cas Cpf1 nucleases in human cells", Nat Biotechnol 34, 869-874 (2016).
Lin et al., "Enhanced homology-directed human genome engineering by controlled timing of CRISPR/Cas9 delivery", Elife 3, e04766, 13 pages (2014).
Maruyama et al., "Increasing the efficiency of precise genome editing with CRISPR-Cas9 by inhibition of nonhomologous end joining", Nat Biotechnol 33, 538-542 (2015).
Meyer and Kircher, "Illumina Sequencing Library Preparation for Highly Multiplexed Target Capture and Sequencing", Cold Spring Harb Protoc 2010, pdb prot5448 (2010).
Nussenzweig and Nussenzweig, "A Backup DNA Repair Pathway Moves to the Forefront", Cell 131, 223-225 (2007).
O'Brien et al., "Investigation of the Alamar Blue (resazurin) fluorescent dye for the assessment of mammalian cell cytotoxicity", Eur J Biochem 267, 5421-5426 (2000).
Pinder et al., "Nuclear domain 'knock-in' screen for the evaluation and identification of small molecule enhancers of CRISPR-based genome editing", Nucleic Acids Res 43, 9379-9392 (2015).
Pinello et al., "Analyzing CRISPR genome-editing experiments with CRISPResso", Nat Biotechnol 34, 695-697 (2016).
Renaud et al., "leeHom: adaptor trimming and merging for Illumina sequencing reads", Nucleic Acids Res 42, e141, 7 pages (2014).
Robert et al., "Pharmacological inhibition of DNA-PK stimulates Cas9-mediated genome editing", Genome Med 7, 93, 11 pages (2015).
Shen et al., "Efficient genome modification by CRISPR-Cas9 nickase with minimal off-target effects", Nat Methods 11, 399-402 (2014).
Shrivastav et al., "DNA-PKcs and ATM co-regulate DNA double-strand break repair", DNA Repair 8, 920-929 (2009).
Song et al., "RS-1 enhances CRISPR/Cas9- and TALEN-mediated knock-in efficiency, Nat Commun 7", 10548 (2016).
Suzuki et al., "In vivo genome editing via CRISPR/Cas9 mediated homology-independent targeted integration", Nature 540, 144-149 (2016).
Wang et al., "Efficient Generation of Orthologous Point Mutations in Pigs via CRISPR-assisted ssODN-mediated Homology-directed Repair", Mol Ther Nucleic Acids 5, e396 (2016).
Yang et al., "Enrichment of G2/M cell cycle phase in human pluripotent stem cells enhances HDR-mediated gene repair with customizable endonucleases", Sci Rep 6, 21264 (2016).
Yu et al., "Small Molecules Enhance CRISPR Genome Editing in Pluripotent Stem Cells", Cell Stem Cell 16, 142-147 (2015).
Zetsche et al., "Cpf1 Is a Single RNA-Guided Endonuclease of a Class 2 CRISPR-Cas System", Cell 163, 759-771 (2015).
Zhang et al., "Efficient precise knockin with a double cut HDR donor after CRISPR/Cas9-mediated double-stranded DNA cleavage", Genome Biol 18, 35, 18 pages (2017).
Khan & La Thangue, "HDAC inhibitors in cancer biology: emerging mechanisms and clinical applications, Immunol", Cell Biol. 90 (2012), 85-94.
Falkenberg and Johnstone, "Histone deacetylases and their inhibitors in cancer, neurological diseases and immune disorders", Nature Rev. Drug Discovery 13 (2014) 673-691.
Nawrocki et al., "MLN4924: a novel first-in-class inhibitor of NEDD8-activating enzyme for cancer therapy", Exp Opin Investing Drugs 21 (2012), 1564-1573.
Le-Trilling et al., "Broad and potent antiviral activity of the NAE inhibitor MLN4924", Sci. Rep. 6 (2016), doi: 19977.
Neher et al., "Novel Irreversible Small Molecule Inhibitors of Replication Protein A Display Single-Agent Activity and Synergize with Cisplatin", Mel. Cancer Ther. 10(2011), 1756-1806.
Shu et al., "Cell cycle G2/M arrest and activation of cyclin-dependent kinases associated with low-dose paclitaxel-induced sub-G1 apoptosis", Apoptosis 2 (1997), 463-470.
Blajeski et al., "G1 and G2 cell-cycle arrest following microtubule depolymerization in human breast cancer cells", J. Clin. Invest. 110 (2002), 91-95.
Mateos-Gomez et al., "Mammalian polymerase θ promotes alternative NHEJ and suppresses recombination", Nature 12 (2015), 254-7.
Pomerantz, Abstract A107: "Development of polymerase theta inhibitors for precision medicine in BRCA-deficient cancers", AACR Mol Cancer Ther 17 (2018), A107.
Harnor et al., "Inhibition of the DNA-Dependent Protein Kinase for Cancer Therapy", Med. Chem (Los Angeles) 7:6 (2017).
Mau-Sorensen et al., "Safety, clinical activity and pharmacological biomarker evaluation of the DNA-dependent protein kinase (DNA-PK) inhibitor M3814: Results from two phase I trials", Annals of Oncology, vol. 29, suppl. 8 (2018) (Abstr.).
Zenke, "M3814: A novel investigational DNA-PK inhibitor to target DNA double strand break repair", Annals of Oncology 29, suppl. 3 (2018), vii654 (Abstr.).
Damstrup et al., "M3814, a DNA-dependent Protein Kinase Inhibitor (DNA-PKi), Potentiates the Effect of Ionizing Radiation (IR) in Xenotransplanted Tumors in Nude Mice", International Journal of Radiation—Oncology-Biology-Physics, vol. 94, Issue 4 (2016), 940-94.
Prakash et al., "Clinically Applicable Inhibitors Impacting Genome Stability", Molecules 23 (2018), 1166, 66 pages.
Ceccaldi et al., "Homologous-recombination-deficient tumours are dependent on Pole-mediated repair", Nature 518 (2015).
Sullivan et al., "Identification of a Small Molecule Inhibitor of RAD52 by Structure-Based Selection", PLoS One (2016), 11 pages.
Chandramouly et al., "Small-Molecule Disruption of RAD52 Rings as a Mechanism for Precision Medicine in BRCA-Deficient Cancers", Chem Biol 22 (2015), 1491-1504.
Extended European Search Report issued in EP18215071.4 dated Jun. 12, 2019, 10 pages.
European Office Action issued in application No. 19 828 736.9-1112 dated Jan. 26, 2024, 7 pgs.
J. R. Mendell et al., "Testing preexisting antibodies prior to AA V gene transfer therapy: rationale, lessons and future considerations", Molecular Therapy, Methods & Clinical Development, vol. Jun. 25, 2022, 10 pgs.
Devkota, S. et al., "The road less traveled: strategies to enhance the frequency of homology-directed repair (HDR) for increased efficiency of CRISPR/Cas-mediated transgenesis," 2018, BMB Rep. 51(9), pp. 437-443, 7 pages.
Gaj, T. et al., "ZFN, TALEN, and CRISPR/Cas-based methods for genome engineering," 2013, Trends in Biotechnology, July, vol. 31, No. 7, pp. 397-405, 9 pages.

(56) References Cited

OTHER PUBLICATIONS

Riesenberg ,S. et al., "Targeting repair pathways with small molecules increases precise genome editing in pluripotent stem cells," Nature Communications, 2018, 9 pages.
Law, J.C. et al., "Mutational in Activation of the p53 Gene in the Human Erythroid Leukemic K562 Cell Line," 1993, Leukemia Research, vol. 17, No. 12, pp. 1045-1050, 6 pages.
Haapaniemi, E. et al., 2018, "CRISPR-Cas9 genome editing induces a p53-mediated DNA damage response," Nature Medicine, vol. 24, pp. 927-930.
Chion, T. M. et al., "Overcoming Pluripotent Stem Cell Dependence on the Repair of Endogenous DNA Damage," 2016, Stem Cell Reports, vol. 6, pp. 44-54, 11 pages.
Mujoo, K. et al., "Differentiation of Human Induced Pluripotent or Embryonic Stem Cells Decreases the DNA Damage Repair by Homologous Recombination," 2017, Stem Cell Reports, vol. 9, pp. 1660-1674, 15 pages.
Luo, X. et al., "CRISPR/Cas9 Ribonucleoprotein Delivery Enhanced by Lipo-Xenopeptide Carriers and Homology-Directed Repair Modulators: Insights from Reporter Cell Lines," 2025, Int. Journal of Molecular Sciences, 26, 4361, 25 pages.
Klein, C. et al., "Overcoming hypoxia-induced tumor radioresistance in non-small cell lung cancer by targeting DNA-dependent protein kinase in combination with carbon ion irradiation," 2017, Radiation Oncology, 12(208), 8 pages.
Peng, R. et al., "Potential pitfalls of CRISPR/Cas9-mediated genome editing," 2016, FEBS Journal 283, pp. 1218-1231, 14 pages.

* cited by examiner

SMALL MOLECULES FOR INCREASING PRECISE GENOME EDITING EFFICIENCY

CROSS REFERENCE TO RELATED APPLICATION

This application is a 35 U.S.C. 371 National Phase Entry Application from PCT/EP2019/086316, filed Dec. 19, 2019, which claims the benefit of European Patent Application No. 18215071.4 filed on Dec. 21, 2021, the disclosure of which is incorporated herein in its entirety by reference.

The instant application contains a Sequence Listing which has been submitted via EFS-Web and is hereby incorporated by reference in its entirety. Said Sequence Listing, created on Dec. 18, 2019, is named D00-18.12.2019-Sequence Listing (P005048348) and is 13.2 kilobytes in size.

The present invention relates to compounds suitable to increase precise genome editing efficiency in a eukaryotic target cell or target organism. Thus, the present invention can be applied in gene therapy.

CRISPR is a bacterial nuclease immune system against viral DNA, which has been adopted to accurately cut chromosomal DNA sequences in eukaryotic cells. Such DNA breaks are repaired by two competing pathways: Non-homologous-End-Joining (NHEJ) or Homology directed Repair (HDR).

In NHEJ, the first proteins to bind to the DNA ends are Ku70/Ku80, followed by DNA protein kinase catalytic subunit (DNA-PKcs) (Shrivastav et al. 2008). The kinase phosphorylates itself and other downstream effectors at the repair site. Recruitment and phosphorylation of several proteins like Artemis result in end-processing ligation by ligase IV (LIG4), X-ray repair cross-complementing protein 4 (XRCC4) and Non-homologous end-joining factor 1 (XLF) (Dueva, Iliakis 2013).

If this canonical NHEJ pathway is repressed, an alternative NHEJ pathway (A-NHEJ) also referred to as microhomology mediated end-joining (MMEJ) becomes active (Nussenzweig & Nussenzweig 2007). It requires Polymerase theta (POLQ), Poly(ADP-ribose)-Polymerase 1 (PARP-1), Werner syndrome ATP-dependent (WRN) helicase and DNA ligase 3 (LIG3) or DNA ligase I (LIG1) amongst other proteins. Binding of the MRN-complex (Mre11, Rad50 and Nbs1) complex to the double strand break (DSB) initiates HDR (Shrivastav et al. 2008). Along with other proteins like DNA endonuclease RBBP8 (CtIP), Bloom helicase (BLM) and Exonuclease 1 (EXO1), terminal nucleotides in the 5' ends are removed, generating long 3' single-stranded DNA (ssDNA) overhangs on both sides of the break of the DNA. These tails are then coated and stabilized by the Replication protein A (RPA) complex, followed by breast cancer 2 (BRCA2) assisted generation of a Rad51 nucleoprotein filament (Shrivastav et al. 2008). Rad52 facilitates replacement of RPA bound to ssDNA with Rad51 and promotes ssDNA annealing (Grimme et al. 2010). Strand invasion with the donor DNA and subsequent DNA synthesis by a polymerase finally results in precisely repaired DNA. The protein kinase ataxia-telangiectasia mutated (ATM) plays a major role in HDR, as it phosphorylates at least 12 repair proteins (Shrivastav et al. 2008).

NHEJ of CRISPR Cas9-induced DSBs is error prone and frequently introduces insertions and deletions (indels) at the cut site. It is therefore useful for knocking out a targeted gene. In contrast, HDR allows precise repair of a DSB by using a homologous donor DNA sequence. If this donor sequence is provided in the experiment and carries mutations, these will be introduced into the genome.

A requirement for a DSB introduced by Cas9 is an NGG sequence (PAM site) in DNA. Targeting of Cas9 is determined by a bound guide RNA (gRNA) which is complementary to 20 nucleotides adjacent to the PAM site. However, the Cas9 nuclease may also cut the genome at sites that carry sequence similarity to those targeted by the gRNA (Fu et al. 2013). Those off-target double stranded cuts mean that unwanted mutations can appear elsewhere in the genome together with the desired mutation.

One strategy to reduce such off-target cuts is to use a mutated Cas9 that introduces single-stranded nicks instead of DSBs such as Cas9 D10A (Shen et al. 2014). Using two gRNAs to introduce two nicks on opposite DNA strands in close proximity to each other will result in a DSB at the desired locus while reducing the risk of two off-target nicks occurring elsewhere in the genome close enough to cause a DSB. Another strategy is to use Cpf1 (Zetsche et al. 2015). This nuclease introduces a staggered cut near a T-rich PAM site and has been shown to produce less off-target effects (Kim et al. 2016) (Kleinstiver et al. 2016).

In current approaches, precise genome editing (PGE) efficiencies, especially for targeted nucleotide substitutions in stem cells, are usually low, ranging from 0.5-15% (Yu et al. 2015) (Gonzalez et al. 2014). Several researchers addressed the low rate of precise genome editing by trying to promote HDR or decrease NHEJ.

Cell cycle synchronization to G2/M phase was shown to increase PGE with single stranded oligodeoxynucleotide (ssODN) donors in HEK293T cells (from 26% to 38%), human primary neonatal fibroblasts (from undetectable to 0.6%) and human embryonic stem cells (hESCs) (from undetectable to 1.6%) (Lin et al. 2014) and with double stranded oligodeoxynucleotide (dsODN) donors in hESCs (from 7 to 41% after sorting) (Yang et al. 2016), since homologous recombination is restricted to this phase and its proteins are upregulated.

Also, improved efficiency was achieved by suppressing key proteins like Ku70/80 and ligase IV with siRNA (from 5 to 25%) or co-expression of adenovirus type 5 proteins 4E1B55K and E4orf6 (from 5 to 36%) in HEK293/TLR cells using dsODN donors (Chu et al. 2015). E1B55K and E4orf6 proteins mediate the ubiquitination and proteosomal degradation of LIG4 among other targets.

A common strategy to increase genome editing has been the use of small molecules. The small molecule ligase IV inhibitor SCR7 has been claimed to block NHEJ and to increase the efficiency of PGE (from 5 to 22.7%) in mouse embryos (Maruyama et al. 2015). Other researchers described similar increase in HEK293/TLR cells, a marginal but significant increase in HEK293A, or found no significant effect in mouse embryos, rabbit embryos and human stem cells (Chu et al. 2015) (Pinder et al. 2015) (Song et al. 2016) (Yang et al. 2016) (Zhang et al. 2017). Recently, Greco et al. reanalysed the structure and inhibitory properties of SCR7 (Greco et al. 2016). They conclude that SCR7 and its derivates are neither selective nor potent inhibitors of human LIG4.

Pharmacological inhibition of DNA-PK, a key protein complex in the NHEJ-pathway, by the small molecules NU7441, KU-0060648 and NU7026 was shown to moderately reduce the frequency of NHEJ and to increase PGE in HEK293/TLR cells (from 1.9 to 3.8%), HEK293 (3 to 7.6%) and human induced pluripotent stem cells (hiPSCs) (from 13 to 16%) with dsODN donors and in mouse embryonic fibroblasts (from 3 to 10%) with ssODN donors (Robert et al. 2015) (Suzuki et al. 2016) (Zhang et al. 2017).

Also, a single small molecule enhancing homologous recombination with CRISPR-Cas9 has been described. The RAD51 stimulatory compound RS-1 increased PGE in rabbit embryos (from 4.4 to 26.1%), HEK293A cells (from 3.5 to 21%) and U2OS cells (from 1.9 to 2.4%)(Song et al. 2016) (Pinder et al. 2015), but not in hiPSCs (Zhang et al., 2017), all with dsODN donors. No effect of RS-1 on PGE efficiency was found in porcine fetal fibroblasts using ssODN donors (Wang et al. 2016).

Furthermore, using a library screen of around 4000 small molecules, Yu et al. found the β3-adrenergic receptor agonist L755507 to increase PGE in hiPSCs (from 0.35 to 3.13%) using ssODN and using dsODN donors in mouse ESCs (from 17.7 to 33.3%), while the repair pathway target of that molecule is not known (Yu et al. 2015). Others did not find significant stimulation of PGE by L755507 in HEK293A cells or hiPSCs (Pinder et al. 2015) (Zhang et al. 2017). Pinder et al. compared SCR7, RS-1 and L755507 singly and together and found no additive effect when adding SCR7 and L755507 together with RS-1 compared to RS-1 alone.

WO 2018/189186 describes that certain compounds when applied as a combination of two or more different compounds selected from inhibitors of histone deacetylase (HDAC) inhibitors of NEDD8 activating enzyme (NAE), inhibitors of DNA-dependent Protein Kinase (DNA-PK) in particular of its catalytic subunit (DNA-PKcs), and inhibitors of replication protein A (RPA) and combinations of compounds selected from these different classes of inhibitors, are capable of increasing genome editing efficiency.

Further, WO 2018/189186 describes that a DNA-PKcs which is catalytically inactive, but structurally intact, increases precise genome editing efficacy, independently from the presence of compounds as indicated above.

The present inventors have found that certain small molecules known as anticancer agents are capable of increasing precise genome editing demonstrate a surprisingly strong increase in homology-directed repair (HDR) efficiency while only exhibiting moderate toxicity. Further, these small molecules were found to be effective under conditions where previously tested small molecules did not exhibit any effect. Thus, these compounds are suitable both in non-medical applications, e.g. as research tool or in medical applications, e.g. for in vivo or ex vivo use.

The invention also relates to the genome editing of human cells in vivo or ex vivo, but it does not relate to subject-matter which is excluded from patentability, such as processes for cloning human beings, processes for modifying the germ line genetic identity of human beings and uses of human embryos for industrial and commercial purposes.

In a first aspect the invention relates to a compound of formula (I)

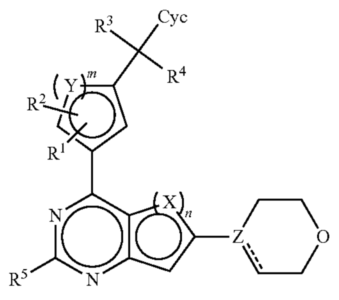

wherein

X is CH, CE, S or N,

Y is CH, $CR^1$, S or N,

Z is C or N,

---- forms, if Z is C, a double bond together with the single bond, is absent if Z is N, n is 1 or 2, where if n=1, X is S, and if n=2, both X are CH, or the X linked to the pyrimidine ring is CF and the X not linked to the pyrimidine ring is CH, or one X is CH and the other X is N;

m is 1 or 2, where if m=1, Y is S, and if m=2, both Y are CH, or one Y is CH and the other is $CR^1$, or one Y is CH and the other Y is N;

$R^1$, $R^2$, $R^3$, $R^4$, independently of one another, are H, Hal, CN, OH, $CONH_2$, CONH(LA) or LA;

$R^5$ is H, Hal, CN or C≡CH;

Cyc is phenyl, which may be unsubstituted, or mono- or disubstituted, independently of one another, by $R^6$, or is $Het^1$;

$Het^1$ is a mono- or bicyclic, 5-10-membered heterocycle, having 1-3 heteroatoms selected from N, O and S atoms, or 1-4 N atoms, which may be unsubstituted or mono-, di- or trisubstituted, independently of one another, by $R^6$, or may be monosubstituted by $Het^2$;

$R^6$ is Hal, LA, oxo, CN, or $NH_2$;

LA is unbranched or branched alkyl having 1-5 C atoms, which may be saturated or partially unsaturated, in which 1-3 H atoms may be replaced by Hal, or one H atom may be replaced by CN or $Het^2$, or one or two $CH_2$ groups may be replaced by O, NH, $N(CH_3)$ or CO;

$Het^2$ is a 3-5-membered aliphatic homo- or heterocycle having 0, 1, 2 or 3 N, O or S atoms, which is unsubstituted; and Hal is F, Cl, Br or I;

or a physiologically acceptable salt or solvate thereof, for use in medicine in a method comprising genome editing in a eukaryotic target cell or in a eukaryotic target organism. In certain embodiments of formula (I), Z is N.

In certain embodiments of formula (I), n is 2 and X is CH.

In certain embodiments of formula (I), n is 2 and one Y is CH and the other Y is $CR^1$.

In certain embodiments of formula (I), $R^1$ and $R^2$ are independently selected from H, and Hal, particularly F or Cl.

In certain embodiments of formula (I), $R^3$ is OH and $R^4$ is H.

In certain embodiments of formula (I), Cyc is $Het^1$, and $Het^1$ is a monocyclic, 6-membered heterocycle, having 1-3, particularly 2 heteroatoms selected from N, O and S atoms, particularly selected from N-atoms which may be unsubstituted or mono-, di- or trisubstituted, by $R^6$, wherein $R^6$ may be Hal, particularly F or Cl, more particularly Cl, or a unbranched or branched alkyl having 1-5 C atoms, which may be saturated or partially unsaturated, in which 1-3 H atoms may be replaced by Hal, or one H atom may be replaced by CN; and wherein $R^6$ is particularly an —O-alkyl having 1-3 C-atoms, more particularly —O—$CH_3$.

The invention also relates to a compound of formula (II)

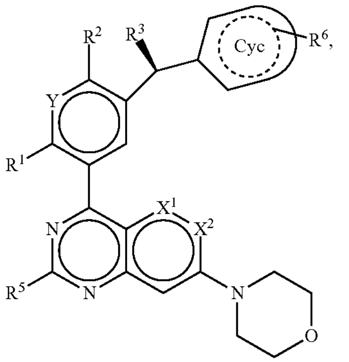

(II)

wherein $R^1$ and $R^2$ are defined as in formula (I), $R^3$ is Hal, CN, OH, $CONH_2$, CON(LA) or LA;

$R^6$ is Hal, LA, oxo, CN, $NH_2$ or $Het^2$;

Hal, LA and $Het^2$ are defined as in formula (I);

$X^1$ is CH, CF or N;

$X^2$ is CH or N, where $X^1$ and $X^2$ are not simultaneously N;

Y is CH or N;

---- denotes the presence or absence of double bonds in Cyc;

or a physiologically acceptable salt or solvate thereof, for use in medicine in a method comprising genome editing in a eukaryotic target cell or in a eukaryotic target organism.

In certain embodiments of formula (II), $X^1$ and $X^2$ are CH.

In certain embodiments of formula (II), n Y is CH.

In certain embodiments of formula (II), $R^1$ is H or F and $R^2$ is H or Cl, and particularly $R^1$ is F and $R^2$ is Cl.

In certain embodiments of formula (II), $R^3$ is OH.

In certain embodiments of formula (I), Cyc is a monocyclic, 6-membered heterocycle, having 2 N-atoms, particularly a pyridazine ring which may be connected at position 3 with the remaining ring system and which is substituted by $R^6$, wherein $R^6$ may be Hal, particularly F or Cl, more particularly Cl, or a unbranched or branched alkyl having 1-5 C atoms, which may be saturated or partially unsaturated, in which 1-3 H atoms may be replaced by Hal, or one H atom may be replaced by CN or $Het^2$, or one or two $CH_2$ groups may be replaced by O, NH, $N(CH_3)$ or CO; and wherein $R^6$ is particularly an —O-alkyl having 1-3 C-atoms, more particularly —O—$CH_3$.

In a particular embodiment the compound of formula (I) and (II) is selected from Nedisertib (M3814) or a physiologically acceptable salt or solvate thereof.

Nedisertib is a compound encompassed by formula (I) and (II) having the structure

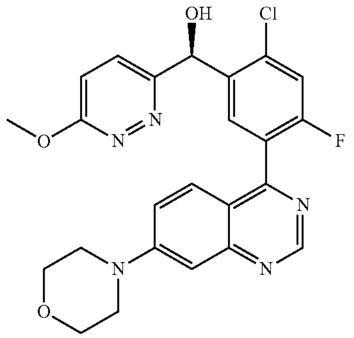 [SMILES: COc1ccc([C@@H](O)c2cc(-c3ncnc4cc(N5CCOCC5)ccc34)c(F)cc2Cl)nn1]

The present inventors have found that Nedisertib (M3814) which is an inhibitor of the DNA-dependent protein kinase catalytic subunit (DNA-PKcs) has an extremely high potency in increasing HDR efficiency in contrast to other known DNA-PKc inhibitors such as NU7026 and NU7441. In particular, the inventors found that administration of M3814 to K562 tumor cells expressing wild-type DNA-PKcs shows a very strong increase in precise genome editing from 18% to 81% while exhibiting only moderate toxicity. In contrast thereto, NU7026 and NU7441 show significantly less precise genome editing efficiency in K562 cells. Corresponding results also were found in human induced pluripotent stem cells. Further, the inventors found that administration of M3814 combination with at least one inhibitor of the microhomology mediated end-joining (MMEJ) pathway and/or at least one inhibitor of the single strand annealing (SSA) pathway may even lead to a synergistic increase in precise genome editing.

Compounds of formula (I) and (II) are described in US 2017/0290836 which is herein incorporated by reference in its entirety. They were found to be inhibitors of serine threonine protein kinases which are suitable for the sensitization of cancer cells to anticancer agents and/or ionizing radiation. It is stated that this effect is caused through specific inhibition of the repair of DNA double strand breaks (non-homologous end-joining). A use of the compounds in genome editing is not described in US 2017/0290836.

A further aspect of the present invention relates to a method for editing the genome of a eukaryotic target cell or a eukaryotic target organism comprising introducing a compound of formula (I) or (II) as defined herein, particularly Nedisertib (M3814), into the target cell or target organism.

Still a further aspect of the present invention relates to the in vitro use of a compound of formula (I) or (II) as defined herein, particularly Nedisertib (M3814), for genome editing in a eukaryotic target cell, particularly in a mammalian target cell, more particularly in a human target cell.

Still a further aspect of the present invention relates to a compound of formula (I) or (II) as defined herein, particularly Nedisertib (M3814), for the use in gene therapy.

In certain embodiments, the compound of formula (I) or (II), particularly Nedisertib (M3814), may be used alone, i.e. as the only active agent in a method comprising genome editing in a eukaryotic target cell or in a eukaryotic target organism. In certain further embodiments, the compound of formula (I) or (11), particularly Nedisertib (M3814), may be used in combination with other active agents in a method comprising genome editing or in gene therapy in a eukaryotic target cell or target cell organism.

In certain embodiments, the compound of formula (I) or (II), particularly Nedisertib, may be used in combination with an inhibitor of histone deacetylase (HDAC), an inhibitor of NEDD8 activating enzyme (NAE) and/or inhibitor of replication protein A (RPA).

HDAC inhibitors are known as cytostatic agents for inhibiting tumor cell proliferation by inducing cell cycle arrest, differentiation and/or apoptosis. HDAC inhibitors usually act by binding to the zinc-containing catalytic domain of HDACs. They may be classified according to the chemical moiety that binds to the zinc ion. Examples of suitable classes of HDAC inhibitors are:

(1) Hydroxamate compounds, (2) Cyclic tetrapeptides and depsipeptides which bind to the zinc ion via a thiol group, (3) Benzamide compounds, (4) Electrophilic ketones and (5) Aliphatic acid compounds.

HDAC inhibitors are reviewed e.g. by Khan & La Thangue (Immunol. Cell Biol. 90 (2012), 85-94) and Falkenberg & Johnstone (Nature Rev. Drug Discovery 13 (2014) 673-691), herein incorporated by reference.

According to the present invention, HDAC inhibitors are preferably selected from synthetic non-nucleosidic compounds, e.g. small molecules having a molecular mass of 1500 Da or less or 1000 Da or less. Specific examples of HDAC inhibitors are selected from Trichostatin A, Vorinostat, Entinostat, Panobinostat, Mocetinostat, Belinostat, Romidepsin, MC1568, Tubastatin A HCI, Givinostat, LAQ824, CUDC-101, Quisinostat 2HCI, Pracinostat, PCI-34051, Droxinostat, PCI-24781, RGFP966, AR-42, Rocilinostat, Valproic acid, C1994, CUDC-907, Tubacin, M344, Resminostat, RG2833, Divalproex Sodium, Scriptaid, Phenylbutyrate, Tubastatin A, CAY10603, Nexturastat A, BG45, LMK-235, Santacruzamate A, BRD73954, HPOB, TMP269, Tasquinimod and 4SC-202 as well as salts or solvates thereof, in particular pharmaceutically acceptable salts or solvates thereof. A preferred HDAC inhibitor is Trichostatin A including salts and solvates thereof.

NAE inhibitors are known as anti-tumor agents as reviewed e.g. by Nawrocki et al. (Exp Opin Investing Drugs 21(2012), 1564-1573) or as antiviral agents as reviewed e.g. by Le-Trilling et al. (Sci. Rep. 6 (2016), doi: 19977), herein incorporated by reference.

According to the present invention, NAE inhibitors are preferably selected from synthetic non-nucleosidic compounds, e.g. small molecules having a molecular mass of 1500 Da or less or 1000 Da or less. A preferred NAE inhibitor is MLN4924 (Pevonedistat) or any salt or solvate thereof, in particular any pharmaceutically acceptable salt or solvate thereof.

RPA inhibitors are known as anti-tumor agents as reviewed e.g. by Neher et al. (Mel. Cancer Ther. 10(2011), 1756-1806), herein incorporated by reference.

According to the present invention, RPA inhibitors are preferably selected from synthetic non-nucleosidic compounds, e.g. small molecules having a molecular mass of 1500 Da or less or 1000 Da or less. Specific examples of RPA inhibitors are NSC15520, TDRL-505 and NSC111847, as well as salts or solvates thereof, in particular pharmaceutically acceptable salts and solvates thereof. A preferred of a RPA inhibitor is NSC15520 including salts and solvates thereof.

The compound of formula (I) or (II), particularly Nedisertib (M3814), may further be used in combination with a compound for synchronizing cells in the G2/M phase such as Nocodazole and ABT-751 (Yang et al., 2016), paclitaxel (Shu et al., Apoptosis 2 (1997), 463-470), or colchicine or vincristine (Blajeski et al., J. Clin. Invest. 110 (2002), 91-95), or salts or solvates thereof. In a further embodiment, the combination may include an Alt-NHEJ inhibitor such as NSC19630 or a salt or solvate thereof.

In further embodiments, the compound of formula (I) or (II), particularly Nedisertib (M3814), may be used in combination with at least one inhibitor of the microhomology mediated end-joining (MMEJ) pathway and/or at least one inhibitor of the single strand annealing (SSA) pathway. Especially preferred is the use of a compound of formula (i) or (II), particularly Nedisertib (M3814), with both at least one inhibitor of the MMEJ pathway and at least one inhibitor of the SSA pathway.

For example, the compound of formula (I) or (II), particularly Nedisertib (M3814), may be used in combination with an inhibitor of the MMEJ pathway, particularly with a knock-down or inhibition of any endogenous polymerase theta (PoIQ) in the target cell or target organism. PoIQ is needed for alternative NHEJ or MMEJ (Mateos-Gomez et al., Nature 518 (2015), 254-7) and has two RAD51 binding domains that inhibit homologous recombination (Ceccaldi et al., Nature 518 (2015), 258-62). A knock-down or inhibition of the endogenous polymerase theta gene in the target cell may be effected, e.g. by CRISPR genome editing, by targeted homologous recombination, by use of RNA interference, e.g. by administering inhibitory RNA molecules such as small interfering RNA molecules (siRNAs), by administering antisense molecules, by transient DNA nicking with a CRISPR enzyme, by administering antibodies against PoIQ and/or by administering small molecule inhibitors (Pomerantz, AACR Mol Cancer Ther 17 (2018), A107).

In particular embodiments, inhibition of PoIQ is carried out by use of RNA interference, e.g. by administering at least one inhibitory RNA molecule such as an siRNA molecule, more particularly by administering at least one inhibitory RNA molecule such as an siRNA molecule which binds to the PoIQ mRNA before the sequence encoding the first RAD51 binding domain and/or a DNA cleavage enzyme adapted for nicking the coding strand of a PoIQ gene or any combination thereof.

Further, the compound of formula (I) or (II), particularly Nedisertib (M3814), may be used in combination with an inhibitor of the RAD52 dependent SSA pathway. A knock-down or inhibition of the endogenous RAD52 gene in the target cell may be effected, e.g. by CRISPR genome editing, by targeted homologous recombination, by use of RNA interference, e.g. by administering inhibitory RNA molecules such as small interfering RNA molecules (siRNAs), by administering antisense molecules, by transient DNA nicking with a CRISPR enzyme, by administering antibodies against PoIQ and/or by administering small molecule inhibitors (Chandramouly et al., Chem Biol 22 (2015), 1491-15044; Sullivan et al., PLoS One 11(2016) e0147230. doi: 10.1371).

In particular embodiments, inhibition of RAD52 is carried out by administering at least one small molecule inhibitor such 6-hydroxy-dopa or a related compound and/or by administering 5-aminoimidazol-4-carboxamide (AICA) or a related compound, e.g. a nucleoside or nucleotide derivative thereof such as AICA ribonucleotide 5'-monophosphate (AICAR).

According to certain embodiments the compound of formula (I) or (II), particularly Nedisertib (M3814), is used alone, i.e. without concomitant use of other active agents, e.g. without a HDAC inhibitor, a NAE inhibitor and a RPA inhibitor. In further embodiments the compound of formula (I) or (II), particularly Nedisertib (M3814), is used without a further DNA-PKcs inhibitor which is different from a compound of formula (I) or (II).

As indicated above, the compound of formula (I) or (II), particularly Nedisertib (M3814), may be used in combination with further active agents. The term "combination" in the context of the present invention encompasses compositions comprising at least two compounds as indicated above together in admixture optionally together with a suitable carrier, e.g. a pharmaceutically acceptable carrier. The term "combination" also encompasses kits comprising at least two compounds as indicated above in separate forms, each optionally together with a suitable carrier, e.g. a pharmaceutically acceptable carrier.

The compound of formula (I) or (II) is suitable for use in genome editing in a eukaryotic target cell, particularly in a eukaryotic target cell as described in the following, including a vertebrate target cell, e.g. an animal target cell such as a mammalian target cell, e.g. a human target cell, but also target cell from non-human animals such as rodents, e.g. mice or zebrafish including a stem cell, e.g. human stem cell, for example an embryonic stem cell or a pluripotent stem cell. In some embodiments, the target cell is a stem cell of a eukaryotic target organism, including an induced or embryonic pluripotent stem cell such as a human induced or embryonic pluripotent stem cell but also an induced or embryonic pluripotent stem cell from non-human animals. In other embodiments, the target cell is a hematopoietic cell or a hematopoietic progenitor cell. In still other embodiments, the target cell is an immortalized cell such as a cancer cell.

In certain embodiments the compound of formula (I) or (II) is used in a method wherein the genome editing comprises introducing a staggered cut, into the doubled-stranded genome of the target cell or target organism. In certain further embodiments, the compound of formula (I) or (II) is used in a method comprising introducing a blunt-ended cut into the double-stranded genome of the target organism.

The compound is intended for use in any type of genome editing including multiplexed genome editing on both chromosomes both in non-medical applications and in medical applications.

The compound of formula (I) or (II) may be used in a genome editing procedure which comprises introducing a staggered cut, or a blunt-ended cut into the genome of the target cell. In order to achieve this result, the target cell may comprise CRISPR/Cas9 enzyme, or a mutated nickase version of CRISPR/Cas9 such as a CRISPR/Cas9 D10A or CRISPR/Cas9 H840A enzyme or a CRISPR/Cpf1 enzyme. Alternatively, other genome editing enzymes, e.g. CRISPRs, transcription activator-like effector-based nucleases (TALENs), zinc finger nuclease proteins, Argonaute of the bacterium *Thermus* thermophiles (TtAgo), recombinases, or meganucleases or other enzymes may be present which provide staggered cuts or blunt-ended cuts in a double stranded target DNA. The present invention is also suitable together with split-fusion versions of the above enzymes, e.g. split-fusion versions of Cas9 or Cas9 D10A (Zetsche et al., 2015).

The enzyme(s) may be introduced into the target cell as such, e.g. as protein or ribonucleoprotein or as nucleic acid molecule encoding the respective enzyme(s). The nucleic acid molecule may be introduced as an expression vector such as a plasmid in operative linkage with appropriate expression control elements for transient or stable expression in the target cell. Suitable transfection techniques for introducing proteins or nucleic acids into the eukaryotic target cells are well known in the art and include lipofection, electroporation, e.g. nucleofection, Ca-phosphate or virus-based methods.

The compound of formula (I) or (II) is suitable for use with all kinds of donor nucleic acid molecules including but not limited to single stranded molecules or double stranded DNA molecules whether amplified in vivo or in vitro or chemically synthesized. The length of the donor nucleic acid molecules is usually in the range of about 20 to 2000 nt or more, e.g. about 80 to 120 nt, 50 to 200 nt or 500 to 2000 nt. The donor nucleic acid molecules are designed to include at least one desired mutation in view of the wild type sequence which is to be introduced into the genome of the target cell by genome editing. The mutation may be a single nucleotide mutation or a mutation encompassing a plurality of nucleotides. In this context, the term mutation refers to a substitution, deletion, or insertion of single nucleotides or of a plurality of nucleotides.

The above aspects comprise a use in vivo, e.g. in isolated cells or cell clusters, but also in vitro, in cells of a target organism. The combinations can be applied in cell types and with genome editing procedures as indicated above, including the use of DNA cleavage enzyme systems capable of introducing a staggered cut, or a blunt-ended cut in a DNA double strand. This aspect also includes a use in medicine including human or veterinary medicine.

Still a further aspect of the present invention is the use of a compound of formula (I) or (II) or a combination comprising a compound of formula (I) or (II) and at least one further active agent in medicine including human or veterinary medicine. An effective dose of the compounds according to the invention, or their salts, solvates or prodrugs thereof is used, in addition to physiologically acceptable carriers, diluents and/or adjuvants for producing a pharmaceutical composition. The dose of the active compounds can vary depending on the route of administration, the age and weight of the patient, the nature and severity of the diseases to be treated, and similar factors. The daily dose can be given as a single dose, which is to be administered once, or be subdivided into two or more daily doses, and is as a rule 0.001-2000 mg. Particular preference is given to administering daily doses of 0.1-500 mg, e.g. 0.1-100 mg.

Suitable administration forms are oral, parenteral, intravenous, transdermal, topical, inhalative, intranasal and sublingual preparations. Particular preference is given to using oral, parenteral, e.g. intravenous or intramuscular, intranasal preparations, e.g. dry powder or sublingual, of the compounds according to the invention. The customary galenic preparation forms, such as tablets, sugar-coated tablets, capsules, dispersible powders, granulates, aqueous solutions, alcohol-containing aqueous solutions, aqueous or oily suspensions, syrups, juices or drops, can be used.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavourings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

Inhalable preparations can present as powders, solutions or suspensions. Preferably, inhalable preparations are in the form of powders, e.g. as a mixture of the active ingredient with a suitable formulation aid such as lactose.

The preparations are produced, aliquoted and sealed under the customary antimicrobial and aseptic conditions.

The compounds of the invention may be administered alone or as a combination therapy with further active agents.

The medical use of the compound of formula (I) or (II) particularly encompasses target gene therapy, e.g. the treatment of disorders associated with an undesired genotype of a patient in need of the treatment. For example, the disorder is a metabolic dysfunction or cancer. By means of the invention, cells from the patient may be subjected to a genome editing procedure in the presence of a combination as described above, thereby increasing the precise genome editing efficiency. This procedure may be carried out in vivo, i.e. by administering the combination to the patient or ex vivo with cells isolated from the patients, which are—after successful genome editing—reimplanted into the patient.

The patient may be a vertebrate animal such as a mammal, preferably a human patient.

Finally, the compound of formula (I) or (II) is also suitable for genome editing in plant cells or plants.

Further, the invention shall be explained in more detail by the following Figures and Examples.

FIGURE LEGENDS

FIG. 1: Homology-directed repair (HDR) efficiencies are increased by M3814. Genome editing efficiencies of the FRMD7 gene with Cas9 and treatment with M3814 for three days are shown. HDR, mix (HDR with indels), NHEJ (non-homologous end joining), and MMEJ (microhomology-mediated end joining with at least two bp of microhomology) are indicated in green, light green, light blue, and light purple, respectively. Error bars show the SEM of three technical replicates for each of two independent experiments.

Figure 2:
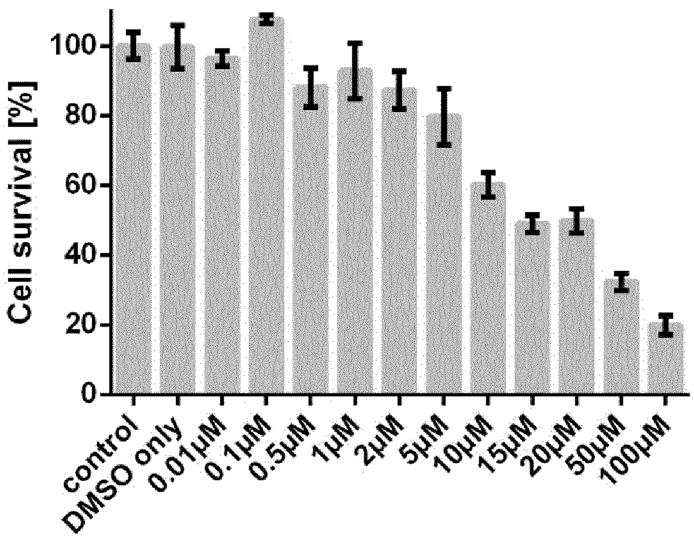

FIG. 2: Cell survival of human immortalized myelogenous leukemia cells K562 cells after treatment with the small molecule M3814. Results of a resazurin assay for cell survival three days after editing are shown. Resazurin is converted into fluorescent resorfin by cellular dehydrogenases and resulting fluorescence (Excitation: 530-570 nm, Emission: 590-620 nm) is a marker for the amount of living cells. Resorfin fluorescence (610±30 nm) of cells without any treatment is set to 100% cell survival. Error bars show the SEM of three technical replicates for three technical replicates.

Figure 3:
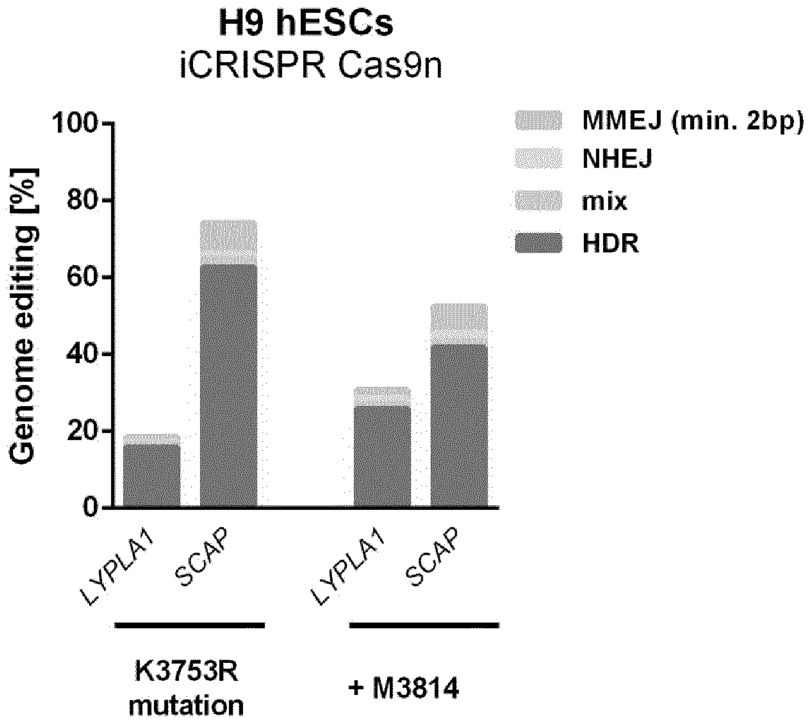

FIG. 3: Increased Homology-directed repair (HDR) efficiencies by M3814 are comparable to what is achievable by total inactivation of DNA-PKcs catalytic active site (K3753R mutation). Genome editing efficiencies of the LYPLA1 and SCAP gene in H9 hESCs-iCRISPR Cas9 nickase (Cas9n) double nicking and treatment with M3814 for three days and with DNA-PKcs K3753R cells are shown. HDR, mix (HDR with indels), NHEJ (non-homologous end joining), and MMEJ (microhomology-mediated end joining with at least two bp of microhomology) are indicated in green, light green, light blue, and light purple, respectively.

Figure 4:
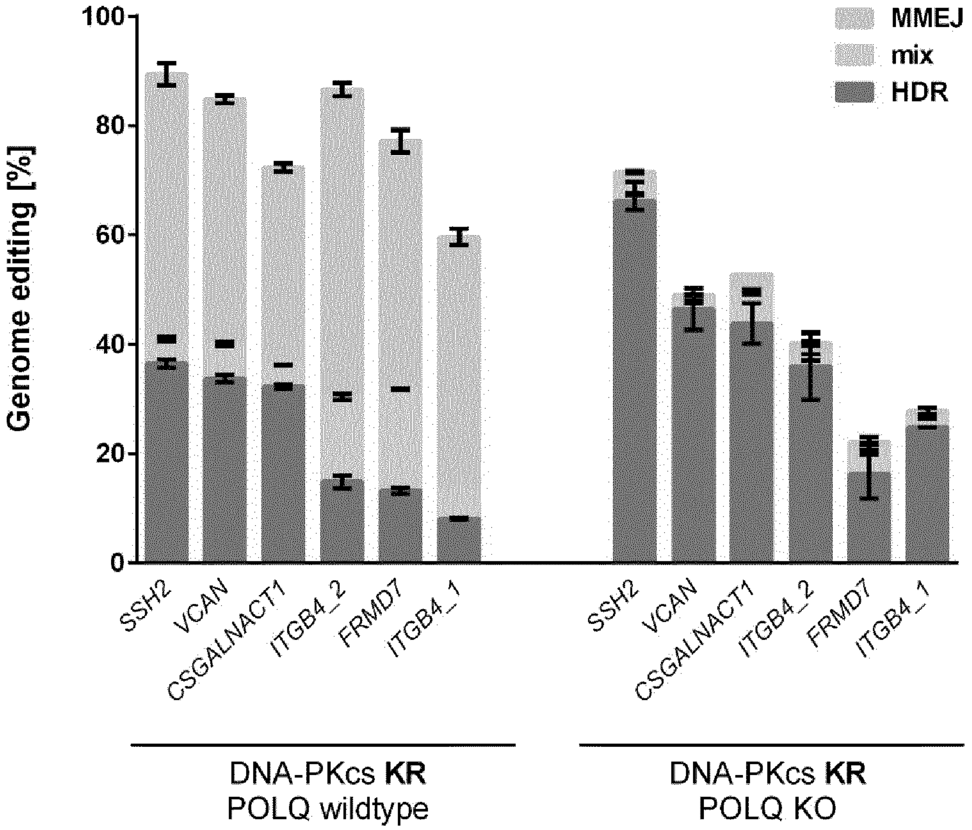

FIG. 4: Residual indels due to MMEJ after NHEJ inactivation can be avoided by inactivation of POLQ leading to quantitative HDR. Shown are genome editing efficiencies in 409B2 hiPSCs-iCRISPR Cas9 nickase (Cas9n) for several genomic targets that have inherently high MMEJ frequencies, which remain after inactivation of NHEJ by the DNA-PKcs K3753R mutation (which can be also achieved by M3814). Additional inactivation of POLQ by introduction of a stop codon in the gene results in further increased HDR. HDR, mix (HDR with indels), and MMEJ (microhomology-mediated end are indicated in green, light green, and light purple, respectively.

Figure 5:
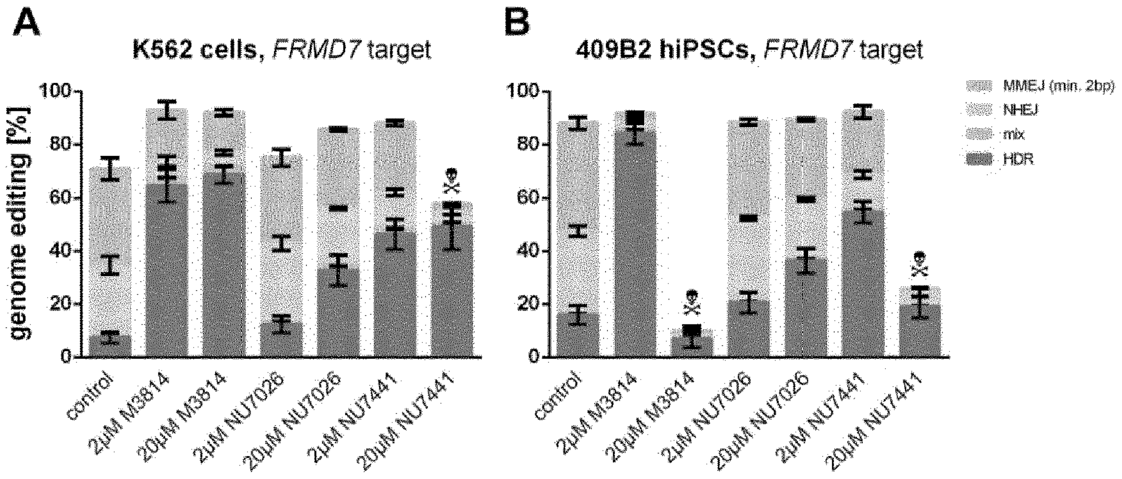

FIG. 5: Comparison of the effect of DNA-PK inhibitors on genome editing efficiency. Editing efficiencies of FRMD7 with Cas9 protein and treatment with different concentrations of M3814, NU7026, and NU7441 are shown for K562 cells (A) and 409B2 hiPSCs (B). HDR, mix (HDR with indels), NHEJ, and MMEJ are indicated in green, light green, light blue and light purple, respectively. Error bars show the SEM of three replicates. A skull indicates excessive cell death of up to around 80% determined by phase contrast light microscopy.

Figure 6:
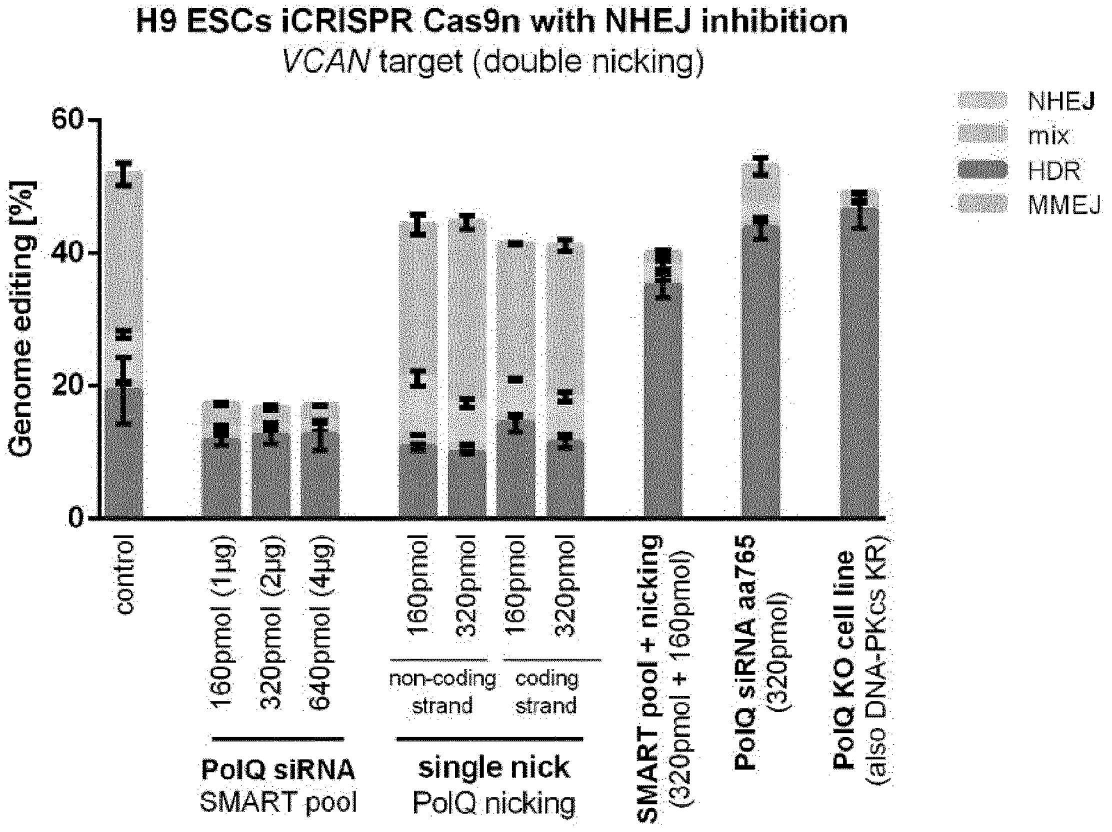

FIG. 6: Inhibition of polymerase theta (PolQ) dependent microhomology mediated end-joining (MMEJ) can further increase HDR if the target of interest is prone to MMEJ repair. All cells have inhibited NHEJ due to the DNA-PKcs KR mutation, which can be transiently achieved by M3814 in wildtype cells as well. Shown are genome editing efficiencies. Cells were treated with different amounts of siRNA against PolQ (Dharmacon ON-TARGET plus Human POLQ (10721) siRNA-SMART pool), single nicking of the first exon of PolQ, a combination of the SMART pool and coding strand nicking, and siRNA against PolQ binding the mRNA at the sequence corresponding to amino acid 765 of PolQ. A cell line with both DNA-PKcs KR and PolQ knockout mutation is shown for comparison. HDR, mix (HDR with indels), NHEJ, and estimated MMEJ (at least 2 bp microhomology) are indicated in green, light green, light blue, and light purple, respectively. Error bars show the SEM of at least two replicates.

Figure 7:
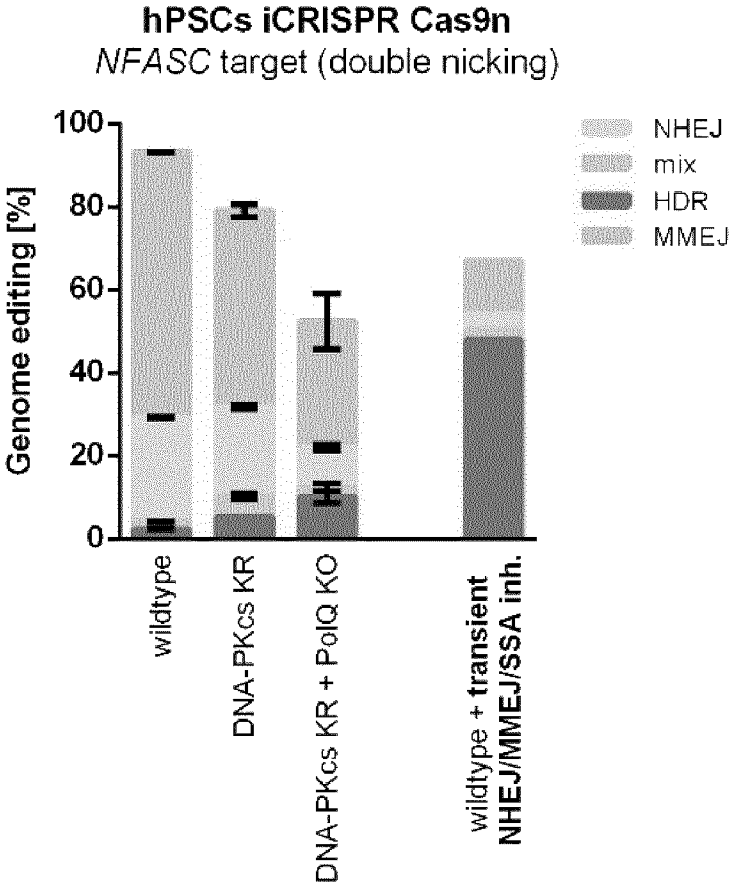

FIG. 7: Inhibition of RAD52 dependent single strand annealing (SSA) together with MMEJ inhibition is needed to further increase HDR for rare targets with long stretches of homology. The NFASC target has an 11 bp stretch of homology. The first three bars show editing efficiencies in a wild-type cell line, a DNA-PKcs KR cell line leading to NHEJ inhibition, and a DNA-PKcs KR+PolQ Knockout cell line leading to NHEJ and MMEJ inhibition. The last bar shows editing efficiencies in a wild-type cell line and transient NHEJ/MMEJ/SSA inhibition achieved by addition of: 2 μM M3814, 320 pmol PolQ siRNA aa765, PolQ coding strand nicking, RAD52 inhibitors (5 μM 6-OH-dopa, 50 μM AICAR). HDR, mix (HDR with indels), NHEJ, and estimated MMEJ/SSA (at least 2 bp microhomology) are indicated in green, light green, light blue, and light purple, respectively. Error bars show the SEM of at least two replicates and one experiment for the last bar.

METHODS

Cell Culture

We recently created an iCRISPR-Cas9n line from human induced pluripotent stem cells (hiPSCs) (409-B2, female, Riken BioResource Center) and human embryonic stem cells (hESCs) (H9) as described by Gonzalez et al. Stem cells were grown on Matrigel Matrix (Corning, 35248) in mTeSR1 medium (StemCell Technologies, 05851) with supplement (StemCell Technologies, 05852) that was replaced daily. K562 cells (ECACC, 89121407) were grown with IMDM (ThermoFisher, 12440053) supplemented with 10% FBS. Cells were grown at 37° C. in a humidified incubator gassed with 5% $CO_2$. Media was replaced every second day for non-pluripotent cell lines. Cell cultures were maintained 4-6 days until ~80% confluency, and subcultured at a 1:6 to 1:10 dilution. Adherent cells were dissociated using EDTA (VWR, 437012C). The media was supplemented with 10 μM Rho-associated protein kinase (ROCK) inhibitor Y-27632 (Calbiochem, 688000) after cell splitting for one day in order to increase cell survival.

Small Molecules

A commercially available small molecule used in this study was M3814 (MedChemExpress, HY-101570). A stock of 100 mM was made using dimethylsulfoxide (DMSO) (Thermo Scientific, D12345). Suitable working solutions for different concentrations were made so that addition of M3814 accounts for a final concentration of 0.05% DMSO in the media.

Design of gRNAs and ssODNs

We designed gRNAs and donors for two nicks per editing site and single-stranded oligodeoxynucleotide DNA donors (ssODNs) carrying the desired amino acid changing mutations. When necessary, the ssODNs carried additional silent non-coding mutations to prevent repeated cutting of the DNA once the targeted substitutions have been introduced (see Table 1).

Oligonucleotide and Ribonucleoprotein Electroporation (Nucleofection)

The recombinant A.s. Cpf1 and S.p. Cas9 protein and electroporation enhancer was ordered from IDT (Coralville, USA) and nucleofection was done using the manufacturer's protocol, except for the following alterations. Nucleofection was done using the B-16 program of the Nucleofector 2b Device (Lonza) in cuvettes for 100 μl Human Stem Cell nucleofection buffer (Lonza, VVPH-5022) containing 1 million cells of the respective lines, 78 pmol electroporation enhancer, 160 pmol of each gRNA (crRNA/tracR duplex for Cas9 and crRNA for Cpf1) (320 pmol for double nicking with both gRNAs for one gene), 200 pmol ssODN donor, 252 pmol CRISPR protein. For editing with the iCRISPR-Cas9n lines only gRNAs and single stranded DNA donors were electroporated. Cells were counted using the Countess Automated Cell Counter (Invitrogen).

Illumina Library Preparation and Sequencing

Three days after editing cells were dissociated using Accutase (SIGMA, A6964), pelleted, and resuspended in 15 μl QuickExtract (Epicentre, QE0905T). Incubation at 65° C. for 10 min, 68° C. for 5 min and finally 98° C. for 5 min was performed to yield ssDNA as a PCR template. Primers for the targeted loci of FRMD7 containing adapters for Illumina sequencing were ordered from IDT (Coralville, USA). PCR was done in a T100 Thermal Cycler (Bio-Rad) using the KAPA2G Robust PCR Kit (Peqlab, 07-KK5532-03) with supplied buffer B and 3 μl of cell extract in a total volume of 25 μl. The thermal cycling profile of the PCR was: 95° C. 3 min; 34× (95° 15 sec, 65° C. 15 sec, 72° C. 15 sec); 72° C. 60 sec. P5 and P7 Illumina adapters with sample specific indices were added in a second PCR reaction (Kircher et al. 2012) using Phusion HF MasterMix (Thermo Scientific, F-531L) and 0.3 μl of the first PCR product. The thermal cycling profile of the PCR was: 98° C. 30 sec; 25× (98° 10 sec, 58° C. 10 sec, 72° C. 20 sec); 72° C. 5 min. Amplifications were verified by size separating agarose gel electrophoresis using EX gels (Invitrogen, G4010-11). The indexed amplicons were purified using Solid Phase Reversible Immobilization (SPRI) beads (Meyer, Kircher 2010). Double-indexed libraries were sequenced on a MiSeq (Illumina) giving paired-end sequences of 2×150 bp. After base calling using Bustard (Illumina) adapters were trimmed using leeHom (Renaud et al. 2014).

Sequence Data Analysis

CRISPResso (Pinello et al. 2016) was used to analyse sequencing data from CRISPR genome editing experiments for percentage of wildtype, targeted nucleotide substitutions (TNS), indels and mix of TNS and indels. Parameters used for analysis were '-w 20', '--min_identity_score 70' and '--ignore_substitutions' (analysis was restricted to amplicons with a minimum of 70% similarity to the wildtype sequence and to a window of 20 bp from each gRNA; substitutions were ignored, as sequencing errors would be falsely characterized as NHEJ-events). Sequence homology for an HDR occurrence was set to 95%. Unexpected substitutions were ignored as sequencing putative errors. Since CRISPResso cannot distinguish reads with indels to be from NHEJ or microhomology-mediated end joining (MMEJ), we wrote a python script to call MMEJ events.

Resazurin Assay

Cells were either seeded with or without editing reagents. The media was supplemented with or without M3814 and each condition was carried out in duplicate. After 72 h media was aspirated and 100 μl fresh media together with 10 μl resazurin solution (Cell Signaling, 11884) was added. Resazurin is converted into fluorescent resorfin by cellular dehydrogenases and resulting fluorescence (Excitation: 530-570 nm, Emission: 590-620 nm) is considered as a linear marker for cell viability (O'Brien et al. 2000). Cells were incubated with resazurin at 37° C. The redox reaction was measured every hour by fluorescence readings using a Typhoon 9410 imager (Amersham Biosciences). After 5 h the fluorescence scan showed a good contrast without being saturated, and was used to quantify the fluorescence using ImageJ and the 'ReadPlate' plugin. Duplicate wells with media and resazurin, but without cells, were used a blank.

Study Design

We aimed to test the precise genome editing efficiency of the small molecule M3814 in K562 and H9 hES cells.

TABLE 1

Oligonucleotides used in this study.

| | | | |
|---|---|---|---|
| gRNAs | LYPLA1 t1 | TGAACGTGGCTATGCCTTCA | (SEQ ID NO: 1) |
| | LYPLA1 t2 | ACAGGCCTAACAGGCCTACA | (SEQ ID NO: 2) |

TABLE 1-continued

| Oligonucleotides used in this study. | | | |
|---|---|---|---|
| | SCAP1 t1 | CTCTGGGATCAGGAGCTTGG | (SEQ ID NO: 3) |
| | SCAP t2 | GCTGCACAGGAGACAGGACA | (SEQ ID NO: 4) |
| | SSH2 t1 | CAGATCCTCAGGAGGGCCCA | (SEQ ID NO: 5) |
| | SSH2 t2 | GTGGTCAAACTCCAGCACCT | (SEQ ID NO: 6) |
| | CSGALNACT1 t1 | CTCATCTTATTTCGACCATT | (SEQ ID NO: 7) |
| | CSGALNACT1 t2 | GCCGTTTGAATTCGTGTTTG | (SEQ ID NO: 8) |
| | VCAN t1 | GTTTACTGTTGCCTGATCAT | (SEQ ID NO: 9) |
| | VCAN t2 | CCCTGTGGAATTTAATACTG | (SEQ ID NO: 10) |
| | ITGB4 t1 | GGGTCCTGGGGTGGGCAGAT | (SEQ ID NO: 11) |
| | ITGB4 t2 | CCGCAGCTGGGCAGCCGTGC | (SEQ ID NO: 12) |
| | FRMD7 t1 | AGCCAGCTGAAAGAAGCCCA | (SEQ ID NO: 13) |
| | FRMD7 t2 (also Cas9) | GTGGGCTCTACATAGCTATG | (SEQ ID NO: 14) |
| | PRKDC t1 | GGTCCTCGCCACCCTTCACC | (SEQ ID NO: 15) |
| | PRKDC t2 | GCGCGTGGAGCAGCTCTTCC | (SEQ ID NO: 16) |
| | POLQ t1 | TAGTTGAAATGGGAGTGCAA | (SEQ ID NO: 17) |
| | POLQ t2 | GTCCTGCTGCAGAATCATTC | (SEQ ID NO: 18) |
| ssODNs | SCAP Cas9n | CTTCCTAAGGCCTGGCAGCAGGTCGGTCACTTGCAGACACAACTCCTCCAAG**GA**CCTG**G**TCCCAGAGCTGCACAGGAGACAGGACAAGGCACCTGCTGTGT | (SEQ ID NO: 19) |
| | LYPLA1 Cas9n | ATAAGTAATATAATGTTCTTATTCAATAAGTAAATTCTTACTTACCATGATGGCATAGCCA**T**GTTCATATTTAATGTAACAGGCCTAACAGGCCTACATGGAAAAGAAAAAAC | (SEQ ID NO: 20) |
| | SSH2 Cas9n | ATCTGACCCTGGGCCCTCCTGAGGATCTGGCAAGTGGTCAAACTCCAGCACC**T**TGGGAGCTGGAACAGTGGCATTCTGCTCAGAATGGGACAGTGAGCCAGCCTCA | (SEQ ID NO: 21) |
| | CSGALNACT1 Cas9n | GTTGGCCATGTTGAGCTTTTCATTTTTCACTTTCATGATGGGGCCGAATGG**A**CGAAATAAGA**C**GAGCCGTTTGAATTCGTGTTTGTGGTCCCCTTTGAAGGTGAGCTCATACA | (SEQ ID NO: 22) |
| | VCAN Cas9n | GATAGCAGCATCAGAACAGCAAGTGGCAGCGAGAATTCTTGATTCCAAT**A**ATCAGGCAACAGTAAACCCTGTGGAATTTAATACTGAGGTTGCAACACCAC | (SEQ ID NO: 23) |
| | ITGB4 Cas9n | TGGTGATGCTGCTGTACTCGCTTTGCAGCGGGTGCTGGAAGAGCCCGGCA**T**GGCTGCCCAGCTGCGGGAAGGGTCCTGGGGTGGGCAGATAGGCCAGTCAGAGGG | (SEQ ID NO: 24) |
| | ITGB4 Cas9 | CTCACCCACTAGGAAGGGCTCGGTGGCGCTGGTGTGGGTGGTGGTGATGCTGCTGTACTCGCTTTGCAGCGGGTGCTGGAAGAGCCCGGCATGGCTGCCCAGCTGCGGGAAGGGTCCTGGGGTGGGC | (SEQ ID NO: 25) |
| | FRMD7 Cas9n | AGGTGCCCAGATGGTCCCCAATTAGAGCAGAGGAAAGGACAAGTCCAGATAGCTATGTAGAGCCCACTGCAATGAAGCCAGCTGAAAGAAGCCCAAGGAATATCAGAATG | (SEQ ID NO: 26) |
| | FRMD7 Cas9 | TATGCCTCCCCAGGTCTTTTTTTATGTGGACAAGCCACCCCAGGTGCCCAGATGGTCCCCAATTAGAGCAGAGGAAAGGACAAGTCCA**G**ATAGCTATGTAGAGCCCACTGCAATGAAGCCAGCTGAA | (SEQ ID NO: 27) |
| | PRKDC Cas9n | GCGAAGGCCCAAGCGCATCATCATCCGTGGCCATGACGAGAGGGAACACCCTTTCCTGGTGA**GA**GGTGGCGAGGACCTGCGGCAGGACCAGCGCGTGGAGCAGCTCTTCCAGGTCATGAATGGGATCCTGGCCCAAG | (SEQ ID NO: 28) |
| | POLQ Cas9n | TGAGTCAATGAGCATGTACTAGAATGTAACAGGGCACATGGATT *CCA*TTGTT**A**TCCCATTTCAACTAAGTCCTGCTGCAGAATCATTC *TGG*CTTCTTCCACTA | (SEQ ID NO: 29) |
| Primers | SCAP forward | AAGCGTTCCCAGTCATTCTG | (SEQ ID NO: 30) |
| | SCAP reverse | CTTTGGCGATACCAGAGAGC | (SEQ ID NO: 31) |
| | LYPLA1 forward | **AAAAA**CTGCTGTACACAAAAGCA | (SEQ ID NO: 32) |
| | LYPLA1 reverse | TGTGTAGGTCTCAAGCAATTATCTG | (SEQ ID NO: 33) |
| | SSH2 forward | TCAGGACTCCTTCCTGCTGT | (SEQ ID NO: 34) |

TABLE 1-continued

| Oligonucleotides used in this study. | | |
|---|---|---|
| SSH2 reverse | GCACCAAAAGGGAAAAGTGA | (SEQ ID NO: 35) |
| VCAN forward | GGCAGGATTCCACGATAGCA | (SEQ ID NO: 36) |
| VCAN reverse | CGTGCCTTCCACTGACTCTT | (SEQ ID NO: 37) |
| CSGALNACT1 forward | GATGCTGTCAGTGGTCAGGA | (SEQ ID NO: 38) |
| CSGALNACT1 reverse | TCTTACCGTGCAAAGAAGGAG | (SEQ ID NO: 39) |
| ITGB4 forward | CCATAGAGTCCCAGGATGGA | (SEQ ID NO: 40) |
| ITG84 reverse | GTGCTCACCCACTAGGAAGG | (SEQ ID NO: 41) |
| FRMD7 forward | TGCTCCTACCGCTAGTCCTG | (SEQ ID NO: 42) |
| FRMD7 reverse | GGTATTATGCCTCCCCAGGT | (SEQ ID NO: 43) |
| PRKDC forward | CTAGCCTGTGCCCTGAGATG | (SEQ ID NO: 44) |
| PRKDC reverse | GCACAACGCTATAGGTCCTCA | (SEQ ID NO: 45) |
| POLQ forward | TTCCAAAATCCTCATGCACA | (SEQ ID NO: 46) |
| POLQ reverse | TGCTGATCAGTTTTGCTCCTT | (SEQ ID NO: 47) |
| Illumina adapter forward 5' | ACACTCTTTCCCTACACGACGCTCTTCCGATCT | (SEQ ID NO: 48) |
| Illumina adapter reverse 5' | GTGACTGGAGTTCAGACGTGTGCTCTTCCGATCT | (SEQ ID NO: 49) |
| VCAN gRNA1 | GTTTACTGTTGCCTGATCAT | (SEQ ID NO: 50) |
| VCAN gRNA2 | CCCTGTGGAATTTAATACTG | (SEQ ID NO: 51) |
| VCAN donor ssDNA | GATAGCAGCATCAGAACAGCAAGTGGCAGCGAGAATTCTTGATTCCAATAATCAGGC AACAGTAAACCCTGTGGAATTTAATACTGAGGTTGCAACACCAC | (SEQ ID NO: 52) |
| NFASC gRNA1 | TGTAGTAGTTGTGGCGACGG | (SEQ ID NO: 53) |
| NFASC gRNA2 | TGCTGCCGCCACCACCACCA | (SEQ ID NO: 54) |
| NFASC donor ssDNA | GGATTCGTGTATCTTAGTCCCGGAGGTGGTGGTGGGAGGACTCTCCGTGGTTGTGGT GGTGGCAGCAGTGGTTGTAGTAGTTGTGGCGACGGTGGTGGTGGTGGCGA | (SEQ ID NO: 55) |
| PolQ gRNA1 | TAGTTGAAATGGGAGTGCAA | (SEQ ID NO: 56) |
| PolQ gRNA2 (coding strand) | GTCCTGCTGCAGAATCATTC | (SEQ ID NO: 57) |
| PolQ KO donor ssDNA | TGAGTCAATGAGCATGTACTAGAATGTAACAGGGCACATGGATTCCATTGTTATCCC ATTTCAACTAAGTCCTGCTGCAGAATCATTCTGGCTTCTTCCACTA | (SEQ ID NO: 58) |
| PolQ siRNA SMART pool | CAACAACCCTTATCGTAAA | (SEQ ID NO: 59) |
| | CGACTAAGATAGATCATTT | (SEQ ID NO: 60) |
| | ACACAGTAGGCGAGAGTAT | (SEQ ID NO: 61) |
| | CCTTAAGACTGTAGGTACT | (SEQ ID NO: 62) |
| PolQ siRNA aa765 | TTGGAAAATACTGTAATCATCCCTGCA | (SEQ ID NO: 63) |

gRNA (crRNA target), single stranded DNA donors (ssODNs) for editing and primers for analysis are shown.
Mutations are in bold letters and ancestral mutations (or inactivating mutation, respectively) are underlined as well.

Results

Effect of M3814 on Precise Genome Editing

We tested the potency of the DNA-PKcs small molecule inhibitor M3814 to increase HDR after a Cas9 or Cas9n induced DSB, even though several small molecule inhibitors of DNA-PK have been described to moderately increase HDR. We show that transient treatment of K562 cells expressing wild-type DNA-PKcs with M3814 has a strong HDR-increasing effect (18% to 81%) (FIG. 1) while only exhibiting moderate toxicity (FIG. 2). We furthermore show that increased HDR efficiencies by M3814 are comparable to what is achievable by total inactivation of the DNA-PKcs catalytic active site (K3753R mutation) (FIG. 3). Also, residual indels due to MMEJ after NHEJ inactivation can be avoided by inactivation of POLQ leading to quantitative HDR (FIG. 4).

We further compared the potency of M3814 and other DNA-PKcs small molecule inhibitors NU7026 and NU7441 to increase HDR after a Cas9 induced DSB. We show that transient treatment of K562 cells expressing wild-type DNA-PKcs with 2 μM and 20 μM M3814 has a stronger HDR-increasing effect than treatment with NU7026 and NU7441 at the same concentrations (FIG. 5A). We furthermore show that strongly increased HDR efficiencies by M3814 are also obtained in human induced pluripotent stem cells (hiPCs) 409B2 at a concentration of 2 μM whereas treatment with NU7026 and NU7441 at the same concentration resulted in much lower efficiencies (FIG. 5B).

Further Increasing HDR by Inhibition of MMEJ and/or SSA Together with Inhibition of NHEJ by M3814

For many targets NHEJ inhibition by the surprisingly potent small molecule M3814 results in drastically increased HDR. For some targets HDR is increased but a substantial portion of genome editing events however still consists of indels. These are due to the microhomology mediated end-joining (MMEJ) pathway (also referred to as alternative NHEJ) which can compete with NHEJ and serves as a back-up pathway which relies on short stretches of microhomology at the cleavage site. MMEJ is dependent on Polymerase Theta (PolQ) (Mateos-Gomez et al., Nature, 2015, supra). PolQ has two RAD51 binding domains that inhibit homologous recombination (Ceccaldi et al., Nature, 2015, supra). We found that siRNAs against PolQ decrease indels with MMEJ signature but do not necessarily always increase HDR (FIG. 6). The PolQ siRNA SMART pool (Dharmacon ON-TARGET plus Human POLQ (10721)) contains four siRNAs that bind the mRNA downstream of the first RAD51 binding domain. We speculated that the PolQ mRNA is partially translated into a truncated protein containing the RAD51 binding domain that prevents an HDR increase. We also tested transient nicking of the first exon of PolQ (before the first RAD51 binding domain) to prevent mRNA expression and there is a tendency for increased HDR when the coding strand is nicked as expected. DNA nick repair has very high fidelity so no permanent PolQ editing is expected. Combining SMART pool siRNA and coding strand nicking resulted in a strong increase in HDR with almost no indels, which is comparable to a cell line with DNA-PKcs KR and PolQ knockout. This high HDR can also be achieved by using siRNA aa765 (hs.Ri.POLQ.13.8, IDT DNA Technologies) that binds mRNA before the sequence corresponding to the first RAD51 binding domain.

In some cases the target for genome editing has long homology stretches around the cleavage site. As we show in FIG. 7 this can result in predominant indel formation even in a cell line were NHEJ and MMEJ is completely inhibited. We speculated that indel formation was carried out by the RAD52 dependent single strand annealing pathway (SSA) which uses long stretched of homology. We found that we can achieve a drastic HDR increase when using the RAD52 inhibitors 6-hydroxy-depa and AICAR together with M3814 and RNAs inhibiting PolQ.

REFERENCES

1. Chu, V. T. et al. Increasing the efficiency of homology-directed repair for CRISPR-Cas9-induced precise gene editing in mammalian cells. *Nat Biotechnol* 33, 543-548 (2015).
2. Fu, Y. et al. High-frequency off-target mutagenesis induced by CRISPR-Cas nucleases in human cells. *Nat Biotechnol* 31, 822-826 (2013).
3. Dueva, R. Iliakis G. Alternative pathways of non-homologous end joining (NHEJ) in genomic instability and cancer. *Transl Cancer Res* 2 (2013).
4. Gonzalez, F. et al. An iCRISPR platform for rapid, multiplexable, and inducible genome editing in human pluripotent stem cells. *Cell Stem Cell* 15, 215-226 (2014).
5. Greco, G. E. et al. SCR7 is neither a selective nor a potent inhibitor of human DNA ligase IV. *DNA Repair* (*Amst*) 43, 18-23 (2016).
6. Grimme, J. M. et al. Human Rad52 binds and wraps single-stranded DNA and mediates annealing via two hRad52-ssDNA complexes. *Nucleic Acids Res* 38, 2917-2930 (2010).
7. Huang, F. et al. Identification of specific inhibitors of human RAD51 recombinase using high-throughput screening. *ACS Chem Biol* 6, 628-635 (2011)
8. Kent, W. J. et al. The human genome browser at UCSC. *Genome Res* 12, 996-1006 (2002).
9. Kim, D. et al. Genome-wide analysis reveals specificities of Cpf1 endonucleases in human cells. *Nat Biotechnol* 34, 863-868 (2016).
10. Kircher, M., Sawyer, S. & Meyer, M. Double indexing overcomes inaccuracies in multiplex sequencing on the Illumina platform. *Nucleic Acids Res* 40, e3 (2012).
11. Kleinstiver, B. P. et al. Genome-wide specificities of CRISPR-Cas Cpf1 nucleases in human cells. *Nat Biotechnol* 34, 869-874 (2016).
12. Lin, S., Staahl, B. T., Alla, R. K. & Doudna, J. A. Enhanced homology-directed human genome engineering by controlled timing of CRISPR/Cas9 delivery. *Elife* 3, e04766 (2014).
13. Maruyama, T. et al. Increasing the efficiency of precise genome editing with CRISPR-Cas9 by inhibition of non-homologous end joining. *Nat Biotechnol* 33, 538-542 (2015).
14. Meyer, M. & Kircher, M. Illumina sequencing library preparation for highly multiplexed target capture and sequencing. *Cold Spring Harb Protoc* 2010, pdb prot5448 (2010).
15. Nussenzweig, A. & Nussenzweig, M. C. A backup DNA repair pathway moves to the forefront. *Cell* 131, 223-225 (2007).
16. O'Brien, J., Wilson, I., Orton, T. & Pognan, F. Investigation of the Alamar Blue (resazurin) fluorescent dye for the assessment of mammalian cell cytotoxicity. *Eur J Biochem* 267, 5421-5426 (2000).
17. Pinder, J., Salsman, J. & Dellaire, G. Nuclear domain 'knock-in' screen for the evaluation and identification of small molecule enhancers of CRISPR-based genome editing. *Nucleic Acids Res* 43, 9379-9392 (2015).
18. Pinello, L. et al. Analyzing CRISPR genome-editing experiments with CRISPResso. *Nat Biotechnol* 34, 695-697 (2016).
19. Renaud, G., Stenzel, U. & Kelso, J. leeHom: adaptor trimming and merging for Illumina sequencing reads. *Nucleic Acids Res* 42, e141 (2014)
20. Robert, F., Barbeau, M., Ethier, S., Dostie, J. & Pelletier, J. Pharmacological inhibition of DNA-PK stimulates Cas9-mediated genome editing. *Genome Med* 7, 93 (2015).
21. Shen, B. et al. Efficient genome modification by CRISPR-Cas9 nickase with minimal off-target effects. *Nat Methods* 11, 399-402 (2014).

22. Shrivastav, M., De Haro, L. P. & Nickoloff, J. A. Regulation of DNA double-strand break repair pathway choice. *Cell Res* 18, 134-147 (2008).
23. Shrivastav, M. et al. DNA-PKcs and ATM co-regulate DNA double-strand break repair. *DNA Repair* (*Amst*) 8, 920-929 (2009).
24. Song, J. et al. RS-1 enhances CRISPR/Cas9- and TALEN-mediated knock-in efficiency. *Nat Commun* 7, 10548 (2016).
25. Suzuki, K. et al. In vivo genome editing via CRISPR/Cas9 mediated homology-independent targeted integration. *Nature* 540, 144-149 (2016).
26. Wang, K. et al. Efficient Generation of Orthologous Point Mutations in Pigs via CRISPR-assisted ssODN-mediated Homology-directed Repair. *Mol Ther Nucleic Acids* 5, e396 (2016).
27. Yang, D. et al. Enrichment of G2/M cell cycle phase in human pluripotent stem cells enhances HDR-mediated gene repair with customizable endonucleases. *Sci Rep* 6, 21264 (2016).
28. Yu, C. et al. Small molecules enhance CRISPR genome editing in pluripotent stem cells. *Cell Stem Cell* 16, 142-147 (2015).
29. Zetsche, B. et al. Cpf1 is a single RNA-guided endonuclease of a class 2 CRISPR-Cas system. *Cell* 163, 759-771 (2015).
30. Zhang, J. P. et al. Efficient precise knockin with a double cut HDR donor after CRISPR/Cas9-mediated double-stranded DNA cleavage. *Genome Biol* 18, 35 (2017).

The invention claimed is:

1. A method for editing a genome of a eukaryotic genome editing target cell or a eukaryotic genome editing target organism, the method comprising introducing Nedisertib (M3814) or a physiologically acceptable salt or solvate thereof into the eukaryotic genome editing target cell or the eukaryotic genome editing target organism, wherein the eukaryotic genome editing target cell or the eukaryotic target genome editing organism comprises a DNA cleavage enzyme selected from the group consisting of a CRISPR/Cas9 enzyme, a mutated nickase version of CRISPR/Cas9, a CRISPR/Cpf1 enzyme, or a split-fusio version of any of the foregoing, wherein introducing the Nedisertib (M3814) or the physiologically acceptable salt or solvate thereof results in an increase in homologous recombination (HDR)-mediated genome-editing efficiency that is greater than that achieved by treatment with known DNA-PKcs inhibitors under equivalent conditions.

2. The method according to claim 1, wherein the genome editing target cell is a vertebrate genome editing target cell.

3. The method according to claim 1, wherein the genome editing target cell is a mammalian genome editing target cell.

4. The method according to claim 3, wherein said mammalian cell is a rodent genome editing target cell or a human genome editing target cell.

5. The method according to claim 1, wherein the genome editing target cell is a stem cell including an induced or embryonic pluripotent stem cell of a eukaryotic genome editing target organism.

6. The method according to claim 5, wherein the induced or embryonic pluripotent stem cell of a eukaryotic genome editing target organism is a human induced or embryonic pluripotent stem cell.

7. The method according to claim 1, wherein the genome editing target organism is a mammalian genome editing target organism.

8. The method according to claim 1, further comprising introducing at least one further compound different from Nedisertib (M3814) or a physiologically acceptable salt or solvate thereof, into said eukaryotic genome editing target cell or said eukaryotic genome editing target organism.

9. The method according to claim 8, wherein the at least one further compound is selected from the group consisting of:

(a) a HDAC inhibitor, (b) a NAE inhibitor, (c) a RPA inhibitor, and (d) a combination of at least 2 of compounds (a), (b) and/or (c).

10. The method according to claim 9, wherein the compound (a) is Trichostatin A, the compound (b) is MLN4924, and/or the compound (c) is NSC15520.

11. The method according to claim 8, wherein the at least one further compound is selected from the group consisting of an inhibitor of the microhomology mediated end-joining (MMEJ) pathway and an inhibitor of the single strand annealing (SSA) pathway.

12. The method according to claim 11, wherein the inhibitor of the MMEJ pathway is selected from the group consisting of an inhibitory RNA molecule directed against the PolQ mRNA, a DNA cleavage enzyme adapted for nicking the coding strand of a PolQ gene and a combination thereof.

13. The method according to claim 12, wherein the inhibitory RNA molecule directed against the PolQ mRNA is an inhibitory RNA molecule which binds to the PolQ mRNA upstream a sequence encoding a first RAD51 binding domain.

14. The method according to claim 11, wherein the inhibitor of the SSA pathway is selected from 6-hydroxydopa, and 5-aminoimidazol-4-carboxamide (AICA).

15. The method according to claim 14, wherein the 5-aminoimidazol- 4-carboxamide (AICA) is AICA ribonucleotide 5'-monophosphate (AICAR).

16. The method according to claim 1, wherein the genome editing comprises introducing a staggered cut or a blunt-ended cut into the double-stranded genome of the eukaryotic genome editing target cell or the eukaryotic genome editing target organism.

17. The method according to claim 16, wherein the staggered cut is a staggered cut with 5' overhangs.

18. The method according to claim 1, wherein the DNA cleavage enzyme is a CRISPR/Cas9D10A enzyme.

19. The method according to claim 1, wherein the genome editing further comprises introducing a donor DNA molecule carrying a desired mutation into the genome editing target cell or the genome editing target organism, wherein said donor DNA molecule is a single-stranded or double-stranded DNA molecule.

20. The method according to claim 19, wherein said donor DNA molecule is a single-stranded DNA molecule.

21. The method according to claim 1, wherein said Nedisertib (M3814) or a physiologically acceptable salt or solvate thereof is introduced in combination with a knock-down or inhibition of endogenous Polymerase Theta in the genome editing target cell or the genome editing target organism.

22. The method according to claim 1, wherein the genome of a eukaryotic genome editing target cell or the eukaryotic genome editing target organism is edited in vivo or ex vivo and used in gene therapy.

23. The method of claim 1, wherein introducing the Nedisertib (M3814) or the physiologically acceptable salt or solvate thereof produces HDR-mediated genome-editing efficiency greater than that obtained with NU7026 and NU7441 under equivalent conditions.

24. A method for editing a genome of a eukaryotic genome editing target cell in vitro, the method comprising introducing Nedisertib (M3814) or a physiologically acceptable salt or solvate thereof into the eukaryotic genome editing target cell, wherein the eukaryotic genome editing target cell comprises a DNA cleavage enzyme selected from the group consisting of a CRISPR/Cas9 enzyme, a mutated nickase version of CRISPR/Cas9, a CRISPR/Cpf1 enzyme, or a split-fusion version of any of the foregoing, wherein introducing the Nedisertib (M3814) or the physiologically acceptable salt or solvate thereof produces a homologous recombination (HDR)-mediated genome-editing efficiency greater than that obtained with known DNA-PKcs inhibitors under equivalent conditions.

25. The method according to claim 24, wherein said eukaryotic genome editing target cell is a mammalian genome editing target cell.

26. The method according to claim 24, wherein said mammalian genome editing target cell is a human genome editing target cell.

27. The method of claim 24, wherein introducing the Nedisertib (M3814) or the physiologically acceptable salt or solvate thereof produces HDR-mediated genome-editing efficiency greater than that obtained with NU7026 and NU7441 under equivalent conditions.

* * * * *

SEQUENCE LISTING

```
<160> NUMBER OF SEQ ID NOS: 63

<210> SEQ ID NO 1
<211> LENGTH: 20
<212> TYPE: DNA
<213> ORGANISM: Artificial Sequence
<220> FEATURE:
<223> OTHER INFORMATION: gRNA LYPLA1 t1

<400> SEQUENCE: 1

tgaacgtggc tatgccttca                                                  20


<210> SEQ ID NO 2
<211> LENGTH: 20
<212> TYPE: DNA
<213> ORGANISM: Artificial Sequence
<220> FEATURE:
<223> OTHER INFORMATION: gRNA LYPLA1 t2

<400> SEQUENCE: 2

acaggcctaa caggcctaca                                                  20


<210> SEQ ID NO 3
<211> LENGTH: 20
<212> TYPE: DNA
<213> ORGANISM: Artificial Sequence
<220> FEATURE:
<223> OTHER INFORMATION: gRNA SCAP1 t1

<400> SEQUENCE: 3

ctctgggatc aggagcttgg                                                  20


<210> SEQ ID NO 4
<211> LENGTH: 20
<212> TYPE: DNA
<213> ORGANISM: Artificial Sequence
<220> FEATURE:
<223> OTHER INFORMATION: gRNA SCAP t2

<400> SEQUENCE: 4

gctgcacagg agacaggaca                                                  20


<210> SEQ ID NO 5
<211> LENGTH: 20
<212> TYPE: DNA
<213> ORGANISM: Artificial Sequence
<220> FEATURE:
<223> OTHER INFORMATION: gRNA SSH2 t1
```

-continued

<400> SEQUENCE: 5
cagatcctca ggagggccca 20

<210> SEQ ID NO 6
<211> LENGTH: 20
<212> TYPE: DNA
<213> ORGANISM: Artificial Sequence
<220> FEATURE:
<223> OTHER INFORMATION: gRNA SSH2 t2

<400> SEQUENCE: 6
gtggtcaaac tccagcacct 20

<210> SEQ ID NO 7
<211> LENGTH: 20
<212> TYPE: DNA
<213> ORGANISM: Artificial Sequence
<220> FEATURE:
<223> OTHER INFORMATION: gRNA CSGALNACT1 t1

<400> SEQUENCE: 7
ctcatcttat ttcgaccatt 20

<210> SEQ ID NO 8
<211> LENGTH: 20
<212> TYPE: DNA
<213> ORGANISM: Artificial Sequence
<220> FEATURE:
<223> OTHER INFORMATION: gRNA CSGALNACT1 t2

<400> SEQUENCE: 8
gccgtttgaa ttcgtgtttg 20

<210> SEQ ID NO 9
<211> LENGTH: 20
<212> TYPE: DNA
<213> ORGANISM: Artificial Sequence
<220> FEATURE:
<223> OTHER INFORMATION: gRNA VCAN t1

<400> SEQUENCE: 9
gtttactgtt gcctgatcat 20

<210> SEQ ID NO 10
<211> LENGTH: 20
<212> TYPE: DNA
<213> ORGANISM: Artificial Sequence
<220> FEATURE:
<223> OTHER INFORMATION: gRNA VCAN t2

<400> SEQUENCE: 10
ccctgtggaa tttaatactg 20

<210> SEQ ID NO 11
<211> LENGTH: 20
<212> TYPE: DNA
<213> ORGANISM: Artificial Sequence
<220> FEATURE:
<223> OTHER INFORMATION: gRNA ITGB4 t1

<400> SEQUENCE: 11
gggtcctggg gtgggcagat 20

<210> SEQ ID NO 12
<211> LENGTH: 20

-continued

<212> TYPE: DNA
<213> ORGANISM: Artificial Sequence
<220> FEATURE:
<223> OTHER INFORMATION: gRNA ITGB4 t2

<400> SEQUENCE: 12
ccgcagctgg gcagccgtgc 20

<210> SEQ ID NO 13
<211> LENGTH: 20
<212> TYPE: DNA
<213> ORGANISM: Artificial Sequence
<220> FEATURE:
<223> OTHER INFORMATION: gRNA FRMD7 t1

<400> SEQUENCE: 13
agccagctga aagaagccca 20

<210> SEQ ID NO 14
<211> LENGTH: 20
<212> TYPE: DNA
<213> ORGANISM: Artificial Sequence
<220> FEATURE:
<223> OTHER INFORMATION: gRNA FRMD7 t2 (also Cas9)

<400> SEQUENCE: 14
gtgggctcta catagctatg 20

<210> SEQ ID NO 15
<211> LENGTH: 20
<212> TYPE: DNA
<213> ORGANISM: Artificial Sequence
<220> FEATURE:
<223> OTHER INFORMATION: gRNA PRKDC t1

<400> SEQUENCE: 15
ggtcctcgcc acccttcacc 20

<210> SEQ ID NO 16
<211> LENGTH: 20
<212> TYPE: DNA
<213> ORGANISM: Artificial Sequence
<220> FEATURE:
<223> OTHER INFORMATION: gRNA PRKDC t2

<400> SEQUENCE: 16
gcgcgtggag cagctcttcc 20

<210> SEQ ID NO 17
<211> LENGTH: 20
<212> TYPE: DNA
<213> ORGANISM: Artificial Sequence
<220> FEATURE:
<223> OTHER INFORMATION: gRNA POLQ t1

<400> SEQUENCE: 17
tagttgaaat gggagtgcaa 20

<210> SEQ ID NO 18
<211> LENGTH: 20
<212> TYPE: DNA
<213> ORGANISM: Artificial Sequence
<220> FEATURE:
<223> OTHER INFORMATION: gRNA POLQ t2

<400> SEQUENCE: 18
gtcctgctgc agaatcattc 20

<210> SEQ ID NO 19
<211> LENGTH: 101
<212> TYPE: DNA
<213> ORGANISM: Artificial Sequence
<220> FEATURE:
<223> OTHER INFORMATION: ssODNs SCAP Cas9n

<400> SEQUENCE: 19
cttcctaagg cctggcagca ggtcggtcac ttgcagacac aactcctcca aggacctggt 60
cccagagctg cacaggagac aggacaaggc acctgctgtg t 101

<210> SEQ ID NO 20
<211> LENGTH: 113
<212> TYPE: DNA
<213> ORGANISM: Artificial Sequence
<220> FEATURE:
<223> OTHER INFORMATION: ssODNs LYPLA1 Cas9n

<400> SEQUENCE: 20
ataagtaata taatgttctt attcaataag taaattctta cttaccatga tggcatagcc 60
atgttcatat ttaatgtaac aggcctaaca ggcctacatg gaaaagaaaa aac 113

<210> SEQ ID NO 21
<211> LENGTH: 106
<212> TYPE: DNA
<213> ORGANISM: Artificial Sequence
<220> FEATURE:
<223> OTHER INFORMATION: ssODNs SSH2 Cas9n

<400> SEQUENCE: 21
atctgaccct gggccctcct gaggatctgg caagtggtca aactccagca ccttgggagc 60
tggaacagtg gcattctgct cagaatggga cagtgagcca gcctca 106

<210> SEQ ID NO 22
<211> LENGTH: 113
<212> TYPE: DNA
<213> ORGANISM: Artificial Sequence
<220> FEATURE:
<223> OTHER INFORMATION: ssODNs CSGALNACT1 Cas9n

<400> SEQUENCE: 22
gttggccatg ttgagctttt catttttcac tttcatgatg gggccgaatg gacgaaataa 60
gacgagccgt ttgaattcgt gtttgtggtc ccctttgaag gtgagctcat aca 113

<210> SEQ ID NO 23
<211> LENGTH: 101
<212> TYPE: DNA
<213> ORGANISM: Artificial Sequence
<220> FEATURE:
<223> OTHER INFORMATION: ssODNs VCAN Cas9n

<400> SEQUENCE: 23
gatagcagca tcagaacagc aagtggcagc gagaattctt gattccaata atcaggcaac 60
agtaaaccct gtggaattta atactgaggt tgcaacacca c 101

<210> SEQ ID NO 24
<211> LENGTH: 105
<212> TYPE: DNA
<213> ORGANISM: Artificial Sequence
<220> FEATURE:
<223> OTHER INFORMATION: ssODNs ITGB4 Cas9n

<400> SEQUENCE: 24
tggtgatgct gctgtactcg ctttgcagcg ggtgctggaa gagcccggca tggctgccca 60
gctgcgggaa gggtcctggg gtgggcagat aggccagtca gaggg 105

<210> SEQ ID NO 25
<211> LENGTH: 127
<212> TYPE: DNA
<213> ORGANISM: Artificial Sequence
<220> FEATURE:
<223> OTHER INFORMATION: ssODNs ITGB4 Cas9

<400> SEQUENCE: 25
ctcacccact aggaagggct cggtggcgct ggtgtgggtg gtggtgatgc tgctgtactc 60
gctttgcagc gggtgctgga agagcccggc atggctgccc agctgcggga agggtcctgg 120
ggtgggc 127

<210> SEQ ID NO 26
<211> LENGTH: 110
<212> TYPE: DNA
<213> ORGANISM: Artificial Sequence
<220> FEATURE:
<223> OTHER INFORMATION: ssODNs FRMD7 Cas9n

<400> SEQUENCE: 26
aggtgcccag atggtcccca attagagcag aggaaaggac aagtccagat agctatgtag 60
agcccactgc aatgaagcca gctgaaagaa gcccaaggaa tatcagaatg 110

<210> SEQ ID NO 27
<211> LENGTH: 127
<212> TYPE: DNA
<213> ORGANISM: Artificial Sequence
<220> FEATURE:
<223> OTHER INFORMATION: ssODNs FRMD7 Cas9

<400> SEQUENCE: 27
tatgcctccc caggtctttt tttatgtgga caagccaccc caggtgccca gatggtcccc 60
aattagagca gaggaaagga caagtccaga tagctatgta gagcccactg caatgaagcc 120
agctgaa 127

<210> SEQ ID NO 28
<211> LENGTH: 137
<212> TYPE: DNA
<213> ORGANISM: Artificial Sequence
<220> FEATURE:
<223> OTHER INFORMATION: ssODNs PRKDC Cas9n

<400> SEQUENCE: 28
gcgaaggccc aagcgcatca tcatccgtgg ccatgacgag agggaacacc ctttcctggt 60
gagaggtggc gaggacctgc ggcaggacca gcgcgtggag cagctcttcc aggtcatgaa 120
tgggatcctg gcccaag 137

<210> SEQ ID NO 29
<211> LENGTH: 103
<212> TYPE: DNA
<213> ORGANISM: Artificial Sequence
<220> FEATURE:
<223> OTHER INFORMATION: ssODNs POLQ Cas9n

<400> SEQUENCE: 29

-continued tgagtcaatg agcatgtact agaatgtaac agggcacatg gattccattg ttatcccatt 60
tcaactaagt cctgctgcag aatcattctg gcttcttcca cta 103

<210> SEQ ID NO 30
<211> LENGTH: 20
<212> TYPE: DNA
<213> ORGANISM: Artificial Sequence
<220> FEATURE:
<223> OTHER INFORMATION: Primer SCAP forward

<400> SEQUENCE: 30
aagcgttccc agtcattctg 20

<210> SEQ ID NO 31
<211> LENGTH: 20
<212> TYPE: DNA
<213> ORGANISM: Artificial Sequence
<220> FEATURE:
<223> OTHER INFORMATION: Primer SCAP reverse

<400> SEQUENCE: 31
ctttggcgat accagagagc 20

<210> SEQ ID NO 32
<211> LENGTH: 23
<212> TYPE: DNA
<213> ORGANISM: Artificial Sequence
<220> FEATURE:
<223> OTHER INFORMATION: Primer LYPLA1 forward

<400> SEQUENCE: 32
aaaaactgct gtacacaaaa gca 23

<210> SEQ ID NO 33
<211> LENGTH: 25
<212> TYPE: DNA
<213> ORGANISM: Artificial Sequence
<220> FEATURE:
<223> OTHER INFORMATION: Primer LYPLA1 reverse

<400> SEQUENCE: 33
tgtgtaggtc tcaagcaatt atctg 25

<210> SEQ ID NO 34
<211> LENGTH: 20
<212> TYPE: DNA
<213> ORGANISM: Artificial Sequence
<220> FEATURE:
<223> OTHER INFORMATION: Primer SSH2 forward

<400> SEQUENCE: 34
tcaggactcc ttcctgctgt 20

<210> SEQ ID NO 35
<211> LENGTH: 20
<212> TYPE: DNA
<213> ORGANISM: Artificial Sequence
<220> FEATURE:
<223> OTHER INFORMATION: Primer SSH2 reverse

<400> SEQUENCE: 35
gcaccaaaag ggaaaagtga 20

<210> SEQ ID NO 36
<211> LENGTH: 20

-continued

<212> TYPE: DNA
<213> ORGANISM: Artificial Sequence
<220> FEATURE:
<223> OTHER INFORMATION: Primer VCAN forward

<400> SEQUENCE: 36
ggcaggattc cacgatagca 20

<210> SEQ ID NO 37
<211> LENGTH: 20
<212> TYPE: DNA
<213> ORGANISM: Artificial Sequence
<220> FEATURE:
<223> OTHER INFORMATION: Primer VCAN reverse

<400> SEQUENCE: 37
cgtgccttcc actgactctt 20

<210> SEQ ID NO 38
<211> LENGTH: 20
<212> TYPE: DNA
<213> ORGANISM: Artificial Sequence
<220> FEATURE:
<223> OTHER INFORMATION: Primer CSGALNACT1 forward

<400> SEQUENCE: 38
gatgctgtca gtggtcagga 20

<210> SEQ ID NO 39
<211> LENGTH: 21
<212> TYPE: DNA
<213> ORGANISM: Artificial Sequence
<220> FEATURE:
<223> OTHER INFORMATION: Primer CSGALNACT1 reverse

<400> SEQUENCE: 39
tcttaccgtg caaagaagga g 21

<210> SEQ ID NO 40
<211> LENGTH: 20
<212> TYPE: DNA
<213> ORGANISM: Artificial Sequence
<220> FEATURE:
<223> OTHER INFORMATION: Primer ITGB4 forward

<400> SEQUENCE: 40
ccatagagtc ccaggatgga 20

<210> SEQ ID NO 41
<211> LENGTH: 20
<212> TYPE: DNA
<213> ORGANISM: Artificial Sequence
<220> FEATURE:
<223> OTHER INFORMATION: Primer ITGB4 reverse

<400> SEQUENCE: 41
gtgctcaccc actaggaagg 20

<210> SEQ ID NO 42
<211> LENGTH: 20
<212> TYPE: DNA
<213> ORGANISM: Artificial Sequence
<220> FEATURE:
<223> OTHER INFORMATION: Primer FRMD7 forward

<400> SEQUENCE: 42

-continued

```
tgctcctacc gctagtcctg                                                    20


<210> SEQ ID NO 43
<211> LENGTH: 20
<212> TYPE: DNA
<213> ORGANISM: Artificial Sequence
<220> FEATURE:
<223> OTHER INFORMATION: FRMD7 reverse

<400> SEQUENCE: 43

ggtattatgc ctccccaggt                                                    20


<210> SEQ ID NO 44
<211> LENGTH: 20
<212> TYPE: DNA
<213> ORGANISM: Artificial Sequence
<220> FEATURE:
<223> OTHER INFORMATION: Primer PRKDC forward

<400> SEQUENCE: 44

ctagcctgtg ccctgagatg                                                    20


<210> SEQ ID NO 45
<211> LENGTH: 21
<212> TYPE: DNA
<213> ORGANISM: Artificial Sequence
<220> FEATURE:
<223> OTHER INFORMATION: Primer PRKDC reverse

<400> SEQUENCE: 45

gcacaacgct ataggtcctc a                                                  21


<210> SEQ ID NO 46
<211> LENGTH: 20
<212> TYPE: DNA
<213> ORGANISM: Artificial Sequence
<220> FEATURE:
<223> OTHER INFORMATION: Primer POLQ forward

<400> SEQUENCE: 46

ttccaaaatc ctcatgcaca                                                    20


<210> SEQ ID NO 47
<211> LENGTH: 21
<212> TYPE: DNA
<213> ORGANISM: Artificial Sequence
<220> FEATURE:
<223> OTHER INFORMATION: Primer POLQ reverse

<400> SEQUENCE: 47

tgctgatcag ttttgctcct t                                                  21


<210> SEQ ID NO 48
<211> LENGTH: 33
<212> TYPE: DNA
<213> ORGANISM: Artificial Sequence
<220> FEATURE:
<223> OTHER INFORMATION: Primer Illumina adapter forward 5'

<400> SEQUENCE: 48

acactctttc cctacacgac gctcttccga tct                                     33


<210> SEQ ID NO 49
<211> LENGTH: 34
<212> TYPE: DNA
<213> ORGANISM: Artificial Sequence
```

-continued

<220> FEATURE:
<223> OTHER INFORMATION: Primer Illumina adapter reverse 5'

<400> SEQUENCE: 49
gtgactggag ttcagacgtg tgctcttccg atct 34

<210> SEQ ID NO 50
<211> LENGTH: 20
<212> TYPE: DNA
<213> ORGANISM: Artificial Sequence
<220> FEATURE:
<223> OTHER INFORMATION: VCAN gRNA1

<400> SEQUENCE: 50
gtttactgtt gcctgatcat 20

<210> SEQ ID NO 51
<211> LENGTH: 20
<212> TYPE: DNA
<213> ORGANISM: Artificial Sequence
<220> FEATURE:
<223> OTHER INFORMATION: VCAN gRNA2

<400> SEQUENCE: 51
ccctgtggaa tttaatactg 20

<210> SEQ ID NO 52
<211> LENGTH: 101
<212> TYPE: DNA
<213> ORGANISM: Artificial Sequence
<220> FEATURE:
<223> OTHER INFORMATION: VCAN donor ssDNA

<400> SEQUENCE: 52
gatagcagca tcagaacagc aagtggcagc gagaattctt gattccaata atcaggcaac 60
agtaaaccct gtggaattta atactgaggt tgcaacacca c 101

<210> SEQ ID NO 53
<211> LENGTH: 20
<212> TYPE: DNA
<213> ORGANISM: Artificial Sequence
<220> FEATURE:
<223> OTHER INFORMATION: NFASC gRNA1

<400> SEQUENCE: 53
tgtagtagtt gtggcgacgg 20

<210> SEQ ID NO 54
<211> LENGTH: 20
<212> TYPE: DNA
<213> ORGANISM: Artificial Sequence
<220> FEATURE:
<223> OTHER INFORMATION: NFASC gRNA2

<400> SEQUENCE: 54
tgctgccgcc accaccacca 20

<210> SEQ ID NO 55
<211> LENGTH: 107
<212> TYPE: DNA
<213> ORGANISM: Artificial Sequence
<220> FEATURE:
<223> OTHER INFORMATION: NFASC donor ssDNA

<400> SEQUENCE: 55

-continued ggattcgtgt atcttagtcc cggaggtggt ggtgggagga ctctccgtgg ttgtggtggt 60
ggcagcagtg gttgtagtag ttgtggcgac ggtggtggtg gtggcga 107

<210> SEQ ID NO 56
<211> LENGTH: 20
<212> TYPE: DNA
<213> ORGANISM: Artificial Sequence
<220> FEATURE:
<223> OTHER INFORMATION: PolQ gRNA1

<400> SEQUENCE: 56
tagttgaaat gggagtgcaa 20

<210> SEQ ID NO 57
<211> LENGTH: 20
<212> TYPE: DNA
<213> ORGANISM: Artificial Sequence
<220> FEATURE:
<223> OTHER INFORMATION: PolQ gRNA2 (coding strand)

<400> SEQUENCE: 57
gtcctgctgc agaatcattc 20

<210> SEQ ID NO 58
<211> LENGTH: 103
<212> TYPE: DNA
<213> ORGANISM: Artificial Sequence
<220> FEATURE:
<223> OTHER INFORMATION: PolQ KO donor ssDNA

<400> SEQUENCE: 58
tgagtcaatg agcatgtact agaatgtaac agggcacatg gattccattg ttatcccatt 60
tcaactaagt cctgctgcag aatcattctg gcttcttcca cta 103

<210> SEQ ID NO 59
<211> LENGTH: 19
<212> TYPE: DNA
<213> ORGANISM: Artificial Sequence
<220> FEATURE:
<223> OTHER INFORMATION: PolQ siRNA SMART pool

<400> SEQUENCE: 59
caacaaccct tatcgtaaa 19

<210> SEQ ID NO 60
<211> LENGTH: 19
<212> TYPE: DNA
<213> ORGANISM: Artificial Sequence
<220> FEATURE:
<223> OTHER INFORMATION: PolQ siRNA SMART pool

<400> SEQUENCE: 60
cgactaagat agatcattt 19

<210> SEQ ID NO 61
<211> LENGTH: 19
<212> TYPE: DNA
<213> ORGANISM: Artificial Sequence
<220> FEATURE:
<223> OTHER INFORMATION: PolQ siRNA SMART pool

<400> SEQUENCE: 61
acacagtagg cgagagtat 19

-continued

```
<210> SEQ ID NO 62
<211> LENGTH: 19
<212> TYPE: DNA
<213> ORGANISM: Artificial Sequence
<220> FEATURE:
<223> OTHER INFORMATION: PolQ siRNA SMART pool

<400> SEQUENCE: 62

ccttaagact gtaggtact                                        19


<210> SEQ ID NO 63
<211> LENGTH: 27
<212> TYPE: DNA
<213> ORGANISM: Artificial Sequence
<220> FEATURE:
<223> OTHER INFORMATION: PolQ siRNA aa765

<400> SEQUENCE: 63

ttggaaaata ctgtaatcat ccctgca                               27
```